US011562165B2

(12) United States Patent
Arsac et al.

(10) Patent No.: US 11,562,165 B2
(45) Date of Patent: Jan. 24, 2023

(54) METHOD FOR IDENTIFYING BY MASS SPECTROMETRY AN UNKNOWN MICROORGANISM SUBGROUP FROM A SET OF REFERENCE SUBGROUPS

(71) Applicant: BIOMERIEUX, Marcy l'etoile (FR)

(72) Inventors: Maud Arsac, Saint-Chamond (FR); Pierre-Jean Cotte-Pattat, Lagnieu (FR); Victoria Girard, Lyons (FR); Valérie Monnin, Creys-Mepieu (FR)

(73) Assignee: BIOMERIEUX, Marcy l'Etoile (FR)

( * ) Notice: Subject to any disclaimer, the term of this patent is extended or adjusted under 35 U.S.C. 154(b) by 1336 days.

(21) Appl. No.: 15/569,005

(22) PCT Filed: Apr. 21, 2016

(86) PCT No.: PCT/FR2016/050940
§ 371 (c)(1),
(2) Date: Oct. 24, 2017

(87) PCT Pub. No.: WO2016/185108
PCT Pub. Date: Nov. 24, 2016

(65) Prior Publication Data
US 2019/0049445 A1 Feb. 14, 2019

(30) Foreign Application Priority Data
Apr. 24, 2015 (FR) .................................. 1553731

(51) Int. Cl.
*G06K 9/00* (2022.01)
*G16B 40/10* (2019.01)
*G16B 40/20* (2019.01)
*C12Q 1/04* (2006.01)
*G06F 16/28* (2019.01)
*G06K 9/62* (2022.01)
*H01J 49/00* (2006.01)
*H01J 49/16* (2006.01)
*H01J 49/40* (2006.01)

(52) U.S. Cl.
CPC ............ *G06K 9/00496* (2013.01); *C12Q 1/04* (2013.01); *G16B 40/10* (2019.02); *G16B 40/20* (2019.02); *G06F 16/285* (2019.01); *G06K 9/62* (2013.01); *H01J 49/0036* (2013.01); *H01J 49/164* (2013.01); *H01J 49/40* (2013.01)

(58) Field of Classification Search
None
See application file for complete search history.

(56) References Cited

FOREIGN PATENT DOCUMENTS

| EP | 2 600 284 A1 | 6/2013 |
|---|---|---|
| EP | 2 600 385 A1 | 6/2013 |
| EP | 2 648 133 A1 | 10/2013 |

OTHER PUBLICATIONS

Karger et al. Determination of Serotypes of Shiga Toxin-Producing *Escherichia coli* Isolates by Intact Cell Matrix-Assisted Laser Desorption Ionization—Time of Flight Mass Spectrometry. Applied and Environmental Microbiology 2011, vol. 77, No. 3, pp. 896-905 (Year: 2011).*
DeBruyne et al. "Bacterial species identification from MALDI-TOF mass spectra through data analysis and machine learning" Systematic and Applied Microbiology 2001, vol. 34, pp. 20-29 (Year: 2001).*
Bengali et al. "A Rapid MALDI-TOF MS Identification Database at Genospecies Level for Clinical and Environmental Aeromonas Strains" PloS One 2012, 7(10), e48441, pp. 1-6 (Year: 2012).*
Dubois et al. "Performances of the Vitek MS Matrix-Assisted Laser Desorption Ionization—Time of Flight Mass Spectrometry System for Rapid Identification of Bacteria in Routine Clinical Microbiology" Journal of Clinical Microbiology 2012, vol. 50, No. 8, pp. 2568-2576 (Year: 2012).*
Welker et al. "Proteomics for routine identification of microorganisms" Proteomics 2011, 11, 3143-3153 (Year: 2011).*
Lay, Jr., Jackson O., "MALDI-TOF Mass Spectrometry of Bacteria." Mass Spectrometry Reviews, vol. 20, pp. 172-194, 2001.
Kuhnert, Peter, et al., "Identification of Animal Pasteurellaceae by MALDI-TOF Mass Spectrometry," Journal of Microbiological Methods, vol. 89, No. 1, pp. 1-7, 2012.
Rettinger, Anna, et al., "*Leptospira* Spp. Strain Identification By MALDI TOF MS is an Equivalent Tool to 16S rRNA Gene Sequencing and Multi Locus Sequence Typing (MLST)." BMC Microbiology, BioMed Central, Ltd., vol. 12, No. 1, 2012, 14 pages.
Cassagne, Carole, et al., "Mould Routine Identification in the Clinical Laboratory by Matrix-Assisted Laser Desorption Ionization Time-of-Flight Mass Spectrometry," PLoS One, vol. 6, No. 12, pp. e28425, 2011, 9 pages.
Marinach-Patrice, Carine, et al., "Rapid Species Diagnosis for Invasive Candidiasis Using Mass Spectrometry," PLoS One, vol. 5, No. 1, p. e8862-1, 2010, 5 pages.
Villmann, Thomas, et al., "Classification of Mass-Spectrometric Data in Clinical Proteomics Using Learning Vector Quantization Methods," Briefings in Bioinformatics, vol. 9, No. 2, pp. 129-143, 2008.

(Continued)

*Primary Examiner* — Olivia M. Wise
(74) *Attorney, Agent, or Firm* — Oliff PLC

(57) ABSTRACT

A method for identifying by mass spectrometry an unknown microorganism subgroup among a set of reference subgroups, including a step of constructing one knowledgebase and one classifying model per associated subgroup on the basis of the acquisition of at least one set of learning spectra of microorganisms identified as belonging to the subgroups of a group and including: constructing an adjusting model allowing mass-to-charge offsets of the acquired spectra to be corrected on the basis of reference masses-to-charges that are common to the various subgroups; adjusting the masses-to-charges of all of the lists of peaks of the learning spectra and constructing one classifying model per subgroup and the associated knowledgebase on the basis of the adjusted learning spectra.

14 Claims, 11 Drawing Sheets

(56) References Cited

OTHER PUBLICATIONS

Ilina, Elena N., et al., "Application of Matrix-Assisted Laser Desorption / Ionization Time-of-Flight Mass Spectrometry for the Study of Helicobacter Pylori," Rapid Communications in Mass Spectrometry, vol. 24, No. 3, pp. 328-334, 2010.

Walsh, John D., et al., "Rapid Intrinsic Fluorescence Method for Direct Identification of Pathogens in Blood Cultures," MBIO, vol. 4, No. 6, pp. 1-9, 2013.

Freiwald, Anja, et al., "Phylogenetic Classification and Identification of Bacteria By Mass Spectrometry," Nature Protocols, vol. 4, No. 5, pp. 732-742, 2009.

Ziegler, Dominik, et al., "Ribosomal Protein Biomarkers Provide Root Nodule Bacterial Identification By MALDI-TOF MS," Applied Microbiology and Biotechnology, vol. 99, No. 13, pp. 5547-5562, 2015.

Salaun, Stephanie, et al., "Whole-Cell Spectroscopy is a Convenient Tool to Assist Molecular Identification of Cultivatable Marine Bacteria and to Investigate Their Adaptive Metabolism," Talanta, Elsevier, vol. 80, No. 5, pp. 1758-1770, 2010.

Sauer, Sascha, et al., "Classification and Identification of Bacteria by Mass Spectrometry and Computational Analysis," PLoS One, vol. 3, No. 7, p. e2843, 2008, 10 pages.

Wang, Zhengping, et al., "Mass Spectrometric Methods for Generation of Protein Mass Database Used for Bacterial Identification," Analytical Chemistry, vol. 74, No. 13, pp. 3174-3182, 2002.

Jul. 19, 2016 International Search Report issued in International Patent Application No. PCT/FR2016/050940.

Jul. 19, 2016 Written Opinion issued in International Patent Application No. PCT/FR2016/050940.

\* cited by examiner

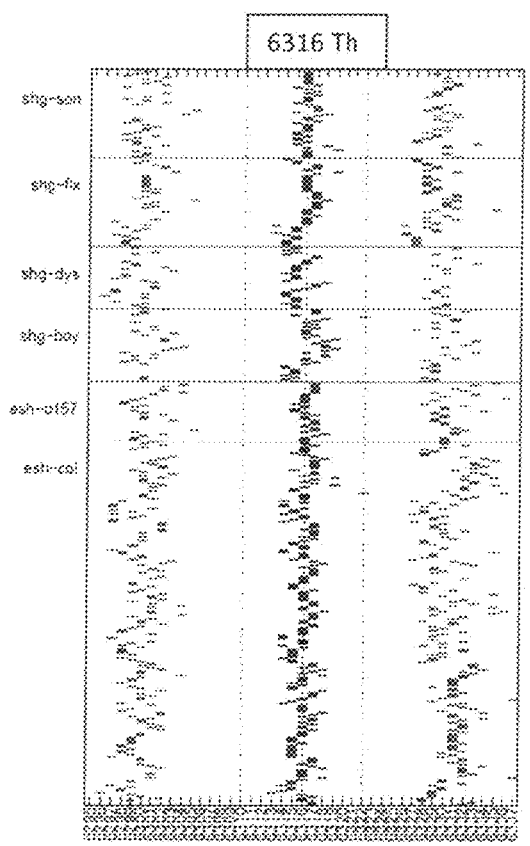
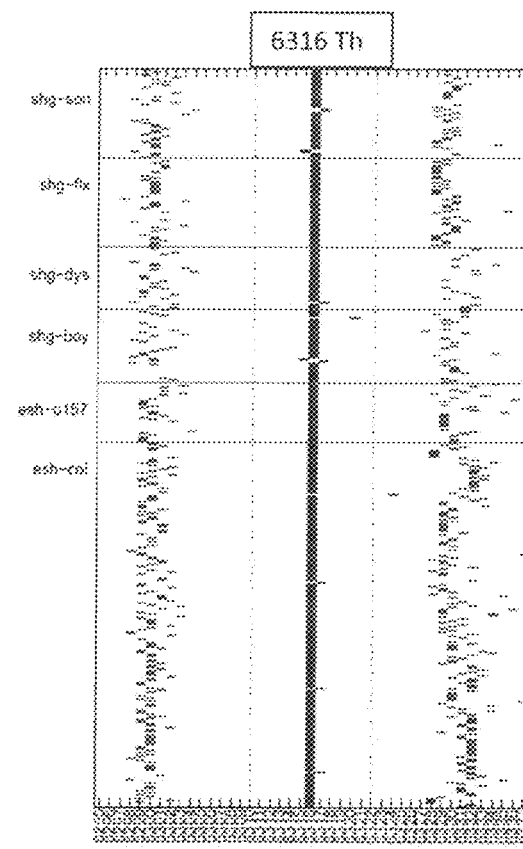
Figure 9a | Figure 9b
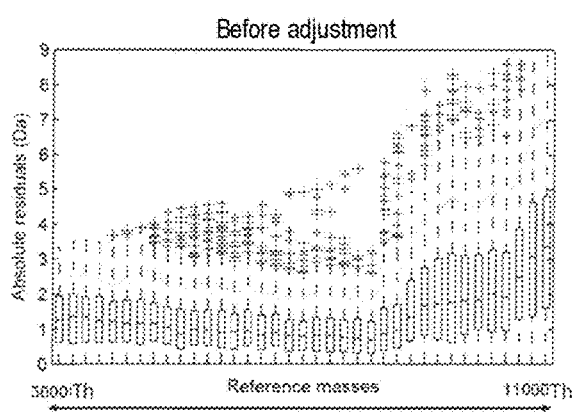
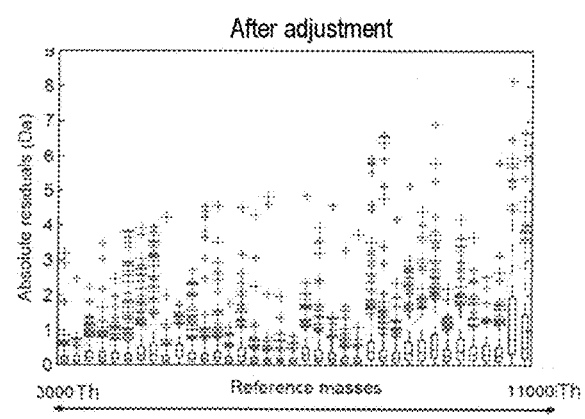
Figure 10a | Figure 10b

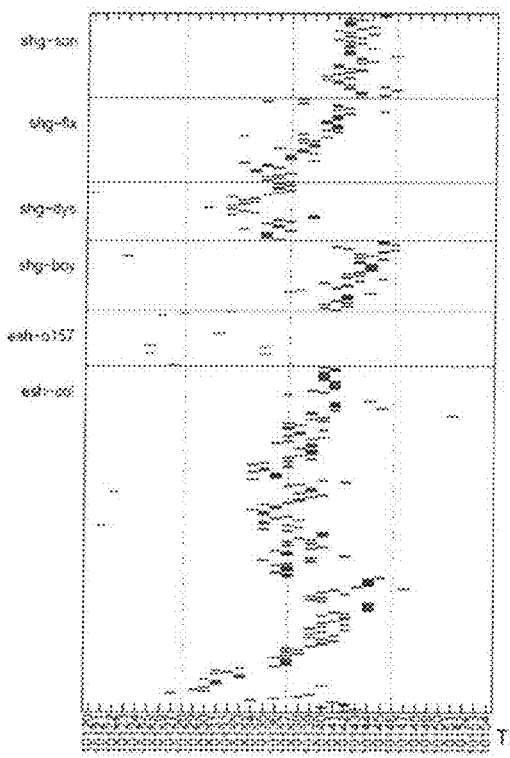 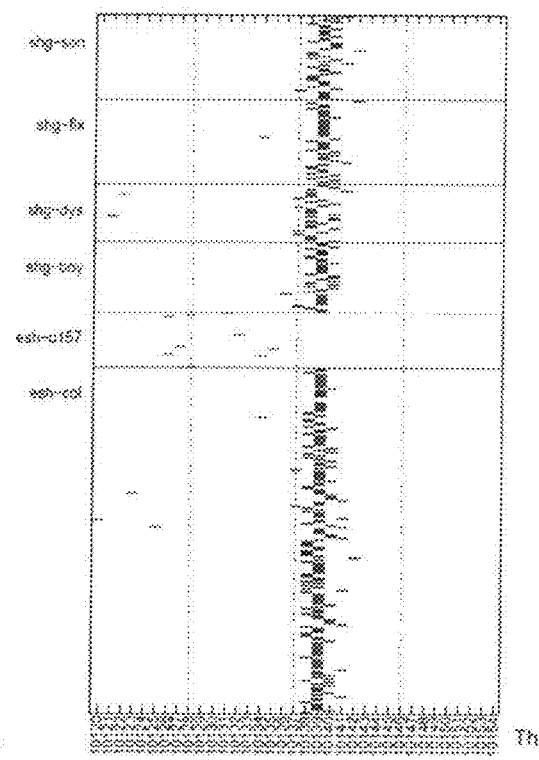
Figure 11a                    Figure 11b
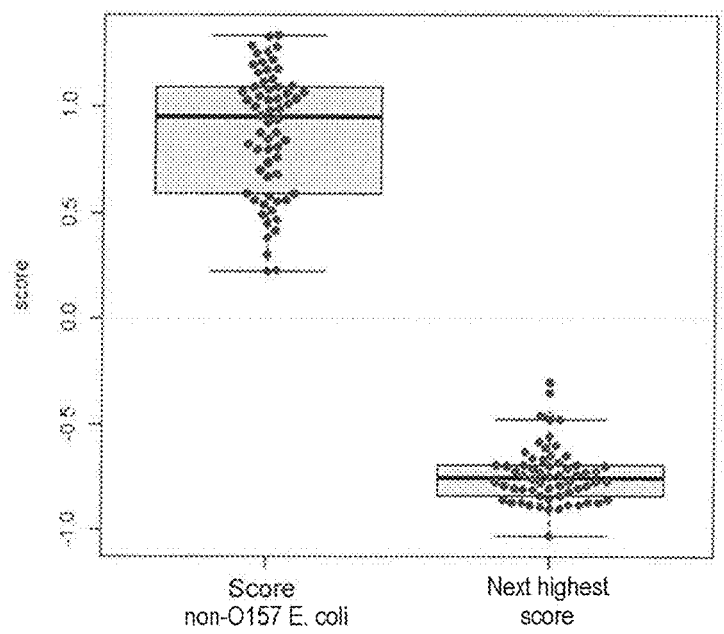
Figure 12

METHOD FOR IDENTIFYING BY MASS SPECTROMETRY AN UNKNOWN MICROORGANISM SUBGROUP FROM A SET OF REFERENCE SUBGROUPS

FIELD OF THE INVENTION

The invention relates to the field of the classification of microorganisms, in particular bacteria, by means of spectrometry. The invention is particularly applicable to the identification of microorganisms by means of mass spectrometry, for example matrix-assisted laser desorption/ionization time-of-flight mass spectrometry (MALDI-TOF MS).

PRIOR ART

It is known to use spectrometry or spectroscopy to identify microorganisms, and more particularly bacteria. To do this, a sample of an unknown microorganism to be identified is prepared then a mass spectrum of the sample is acquired and preprocessed, in particular to remove noise, smooth the signal and subtract the baseline. A step of detecting peaks present in the acquired spectra is then carried out. The peaks of the spectrum thus obtained are then classified using classifying tools associated with data of a knowledgebase constructed from lists of reference peaks, each list being associated with one identified microorganism or one identified group of microorganisms (strain, class, order, family, genus, species, etc.).

More precisely, the identification of microorganisms by classification conventionally consists:

in a first step, of constructing, by way of a supervised learning method, a classifying model associated with a knowledgebase, depending on what are called "learning" mass spectra of microorganisms the groups and more particularly the species of which are known beforehand, the classifying model and the knowledgebase together defining rules distinguishing these various groups;

in a second step, of identifying a particular unknown microorganism by:
  acquiring a mass spectrum of the latter; and
  applying, to the acquired spectrum, the classifying model in relation with the associated knowledgebase, i.e. the model and knowledgebase constructed beforehand, in order to determine at least one group, and more particularly one species, to which the unknown microorganism belongs.

Typically, a mass-spectrometry-based identifying apparatus includes a mass spectrometer and a computer unit for processing information, which is partially or completely integrated into the spectrometer or connected to the latter by way of a communication network (e.g. one or more personal computers, servers, printed circuit boards, digital signal processors (or DSPs), and generally any microprocessor-based system able to receive data, store them, process them and produce as output the processed data, for example with a view to storing them in a computer memory and/or displaying them on a screen, the system possibly itself comprising one or more microprocessor-based units in charge of processing specific data and communicating in them) receiving the measured spectra and implementing the aforementioned second step. Such an identifying apparatus is for example the Vitek® MS sold by the applicant. The first step is for its part implemented by the manufacturer of the apparatus who constructs the knowledgebase and the classifying model and integrates it into the machine before its exploitation by a customer.

Furthermore, certain apparatuses allow their users to update their own knowledgebases and associated classifying models.

In order to acquire a mass spectrum of a sample by MALDI-TOF spectrometry, said sample is deposited on a holder comprising various reception locations, which holder is also called a plate. The sample is then covered with a matrix that allows the sample to crystallize.

In use, a mass-spectrometry-based identifying apparatus must be calibrated regularly in order to guarantee the accuracy and precision of the measurement of the masses-to-charges expected in the analyzed spectrum. Two conventional techniques exist and they are routinely carried out in order to guarantee these parameters.

External calibration is a technique that is routinely carried out on most mass-spectrometry apparatuses. For this technique, a standard mixture (or external calibrator) is deposited in a separate location from that of the sample on the plate holding the sample in the apparatus. External calibration consists in adjusting the mass-to-charge axis (m/z axis) of the mass spectra of the standard mixture, the content of which is known, so that the observed peaks coincide with their theoretical position, a list of reference peaks corresponding to characteristic masses-to-charges having been defined beforehand for this standard. In external calibration, the presence of reference peaks corresponding to these characteristic masses-to-charges is sought in the list of peaks of the spectrum of the standard mixture, with a given tolerance in the expected position. The spectrum of the standard mixture is then realigned depending on the observed position of each of the found reference masses-to-charges. Subsequently, the transformation applied in order to realign the spectrum of the standard mixture is applied to the spectrum of the sample to be analyzed in order to realign its position on the m/z axis.

This method has the advantage that it is possible to work on very small quantities of samples without risk of suppression of the signal. However external calibration is not precise enough for the classification of microorganisms, in particular at taxonomic levels below the species level.

Internal calibration is used to obtain a maximum measurement precision. This technique may be used in addition to external calibration in order to achieve greater precision in the position of the masses-to-charges of the spectrum. This calibration method is qualified internal because a standard mixture (or internal calibrator) is incorporated into the sample to be analyzed before the acquisition. In the context of MALDI-TOF spectrometry, the matrix (α-cyano-4-hydroxycinnamic acid (α-HCCA), etc.) is deposited on both the sample and standard in order to co-crystallize them. Thus, in the analysis of the acquired mass spectrum, the assignment of the known masses-to-charges of the compounds of the standard mixture allows calibration constants to be calculated. These constants are then used to calculate the masses-to-charges of unknown compounds. However, the main drawback of this method is the risk of the signal of analyte ions present in the sample being suppressed because of too high a concentration of standard mixture. In the context of a method for preparing biological samples by tryptic digestion, the positions of the masses-to-charges corresponding to the trypsin may also be used as internal calibrator.

It is known that the identification of certain species or subspecies of microorganisms by MALDI-TOF spectrometry requires a high precision in the acquired spectra in order to differentiate groups of similar species. More particularly, the distinction of similar species and the identification of microorganisms at the subspecies level or the strain level (strains of different serotypes, strains of different pathotypes, strains of different genotypes, etc.) are notoriously complex. Specifically, these subgroups have spectra that are very similar making their distinction impossible with the knowledgebases and classifying algorithms developed for identification at the group level, for example at the next higher taxonomic level. This limit is in particular due to the resolution achieved with mass-spectrometry apparatuses but also to the variability in the spectra acquired on a given apparatus and between different apparatuses. For example, an offset may be observed between the position of the peaks of a number of spectra acquired with a given sample. This offset may for example be seen in spectra acquired for a sample deposited in a single location or in a plurality of locations of the sample holder. This variability leads to uncertainty in the mass-to-charge measurement. Although this does not hinder identification at the group level, it prevents discrimination at levels lower than the group, such as of subgroups (typically at levels lower than the species of the microorganism).

SUMMARY OF THE INVENTION

The objective of the invention is to decrease this variability by improving the precision of the position of the peaks of the mass spectra acquired.

The objective of the invention is also to provide a method that does not modify existing sample-preparation methods and that is able to be used directly with existing protocols, i.e. a method that in particular does not require an additional internal or external standard.

Another objective of the invention is to provide a method allowing microorganism identification at the subgroup level following an identification at the group level.

Thus, one subject of the invention is a method for identifying, by mass spectrometry, the subgroup of an unknown microorganism after the group of the same microorganism has been identified.

For this purpose, the invention relates to a method for identifying by mass spectrometry an unknown microorganism subgroup among a set of reference subgroups, including:

A first step of constructing one knowledgebase and one classifying model per associated group on the basis of a set of learning spectra of microorganisms identified as belonging to said group A second step of constructing one knowledgebase and one classifying model per associated subgroup on the basis of the acquisition of at least one set of learning spectra of microorganisms identified as belonging to said subgroups of the group, comprising:

Constructing an adjusting model allowing mass-to-charge offsets of the acquired spectra to be corrected on the basis of reference masses-to-charges that are common to the various subgroups Adjusting the masses-to-charges of all of the lists of peaks of the learning spectra.

Constructing one classifying model per subgroup and the associated knowledgebase on the basis of the adjusted learning spectra A third step of classifying to a subgroup an unknown microorganism including:

Acquiring at least one spectrum of the unknown microorganism

Classifying into a group said spectrum according to said per-group classifying model and said per-group knowledgebase Adjusting the masses-to-charges of all of the list of peaks of said spectrum according to the adjusting model, allowing mass-to-charge offsets of the spectrum of the unknown microorganism to be corrected Classifying into a subgroup of said group with said per-subgroup classifying model and the per-subgroup knowledgebase The invention thus allows, directly after the group of an unknown microorganism has been identified, the subgroup (subspecies, type of strain etc.) of the same microorganism to be identified by mass spectrometry, all this being achieved without acquiring the mass spectrum of the sample containing the unknown microorganism a second time and without adding an internal standard.

The invention thus has the same effect on the precision of the masses-to-charges as the use of an internal standard, and allows a routine operating mode to be proposed to the user of the mass-spectrometry apparatus that is identical to a simple group-level identification. In addition, the invention proves to be particularly economical in terms of the time required to develop the subgroup-level knowledgebase and to routinely classify unknown microorganisms and cuts out the additional costs of an internal or external standard. Most of the steps of the method according to the invention are also automatable in order to limit the number of interventions required to construct the classifying model and the associated knowledgebase, and to routinely analyze unknown microorganisms.

By group and subgroup, what is meant is a hierarchical representation in tree form of the types of reference microorganisms used in the construction of the knowledgebases, for example in terms of evolution and/or phenotype and/or genotype. The subgroup level always corresponds to a subset of the group. In the case of bacteria, the group may thus be a species in the conventional-analysis-technique sense, a subgroup then possibly being a subspecies of the group or even a particular phenotype of the group. However, a group may also consist of a plurality of species that cannot be distinguished with conventional analysis techniques, each corresponding subgroup thus possibly corresponding to one or more of these species.

Advantageously, a step of optimizing the list of reference masses-to-charges, which is based on the quality of the adjustment obtained following at least one of the adjusting steps, may be carried out.

The reference masses-to-charges that are common to the various subgroups may be identified and selected on the basis of masses-to-charges that are known beforehand or deduced according to statistical criteria of frequency of the presence of the peaks in each of the subgroups of the group.

To do this, the method according to the invention may comprise a step consisting in Discretizing the space of the masses-to-charges of each of the spectra of each subgroup Detecting the presence or absence of peaks around the masses-to-charges defined by the discretizing step according to a tolerance factor Filtering said masses-to-charges depending on the frequency of presence of peaks for each of the subgroups Approximating the position of the retained masses-to-charges The discretizing step may advantageously be carried out over an interval of masses-to-charges that is restricted with respect to the interval of masses-to-charges that is obtained following the acquisition of the spectrum. The approximating step may advantageously consist in seeking a position representative of the distribution of the positions of the peaks present around each of the retained masses-to-charges The identification of the reference masses-to-charges of the method may thus be based on a statistical analysis of the frequency of presence of the peaks of the spectra acquired for the construction of a knowledgebase of the subgroups, both with respect to the development of the classifying model and its routine use.

Advantageously, the method comprises in the step of constructing one knowledgebase and one classifying model per associated subgroup:

Constructing a second adjusting model allowing mass-to-charge offsets of the acquired spectra to be corrected on the basis of reference masses-to-charges that are common to the various subgroups A second step of adjusting the masses-to-charges of all of the lists of peaks of the learning spectra on the basis of the second adjusting model Advantageously, the method comprises a step of controlling the adjustment following at least one of the steps of adjusting the masses-to-charges in the step of constructing one knowledgebase and one classifying model per associated subgroup.

The parameters of the adjusting model(s) may advantageously be obtained with what is called a robust estimating method.

Advantageously, the known reference masses-to-charges that are common to the various subgroups are selected with a step consisting in Detecting the presence or absence of peaks around the reference masses-to-charges according to a tolerance factor Filtering said masses-to-charges depending on the frequency of presence of peaks for each of the subgroups and/or approximating the position of the retained reference masses-to-charges Advantageously, the step of constructing one knowledgebase and one classifying model per associated subgroup comprises a step of discretizing the masses-to-charges of the acquired spectra.

Advantageously, the step of constructing one knowledgebase and one classifying model per associated subgroup comprises a step of processing the intensities of the acquired spectra.

Advantageously, the step of constructing one knowledgebase and one classifying model per associated subgroup comprises a step of controlling the quality of the acquired spectra.

According to one embodiment, the mass spectrometry is MALDI-TOF spectrometry.

Another subject of the invention is a device for identifying a microorganism by mass spectrometry, comprising:
  a mass spectrometer able to produce mass spectra of microorganisms to be identified;
  a computer system able to identify the microorganisms associated with the mass spectra produced by the spectrometer by implementing a method as claimed in any one of the preceding claims.

Another subject of the invention is a device for identifying a microorganism by mass spectrometry, comprising:
  a mass spectrometer able to acquire at least one mass spectrum of a microorganism to be identified;
  a computer system able to identify the microorganism associated with the at least one mass spectrum acquired by the spectrometer, said system comprising:
    a computer memory storing:
      one knowledgebase and one classifying model per group of microorganisms;
      one knowledgebase and one classifying model per subgroup of microorganisms;
      an adjusting model for correcting mass-to-charge offsets of the spectra acquired by the mass spectrometer on the basis of references that are common to the various subgroups of the per-subgroup knowledgebase and classifying model;
      computer instructions for producing a list of peaks on the basis of the acquired mass spectrum;
      computer instructions for classifying the microorganism into a group depending on the produced list of peaks according to said per-group classifying model and said per-group knowledgebase;
      computer instructions for adjusting the list of peaks according to the adjusting model;
      computer instructions for classifying the microorganism into a subgroup depending on the adjusted list of peaks according to said per-subgroup classifying model and said per-subgroup knowledgebase;
    a microprocessor-based computer unit for implementing computer instructions stored in the computer memory so as to classify the microorganism into a group and a subgroup;
    a computer memory for storing the result of the classification and/or a display screen for displaying the result of the classification.

The computer system is partially or completely integrated into the spectrometer or is connected to the latter by way of a communication network, which may or may not be wireless. The system for example comprises one or more personal computers, servers, printed circuit boards, digital signal processors (or DSPs), and generally is a microprocessor-based system able to receive data, store them, process them and produce as output processed data, for example for storage in a computer memory and/or for display on a screen, the system possibly itself comprising one or more microprocessor-based computer units in charge of processing specific data and communicating in them. For example, a first computer unit is integrated into the spectrometer and is in charge of preprocessing the measured signals (e.g. conversion of a time-of-flight signal into a mass-to-charge signal, all or some of the treatment allowing mass spectra to be obtained and/or all or some of the treatment allowing a list of peaks derived from the mass spectra to be obtained), and a second remote computer unit, for example having more substantial computational resources, is connected to the first computer unit in order to carry out the rest of the processing leading to the identification of the microorganism. It may for example be a question of a second computer unit providing a cloud-computing type service. The computer memory is for example a mass storage device (e.g. a hard disk).

The device for identifying a microorganism according to the invention furthermore stores the data and instructions required to implement the third classifying step described above.

For example, the data (knowledgebases, classifying model, adjusting model, etc.) and the instructions are incorporated into a prior-art identifying device that already has available computer resources for implementing the invention. In particular, the invention is implemented by an identifying system comprising a Vitek® MS sold by the applicant.

BRIEF DESCRIPTION OF THE FIGURES

The invention will be better understood on reading the following description, which is given merely by way of example, with reference to the appended drawings, in which:

FIGS. 9a and 9b are a chart of the result of a first adjustment and a second adjustment according to the invention FIGS. 10a and 10b are a chart of the result on the precision of an adjustment according to the invention FIGS. 11a and 11b are a chart of the result on the precision of an adjustment according to the invention FIG. 12 is a chart of the identifying result at the microorganism-subgroup level

DETAILED DESCRIPTION OF THE INVENTION

A method according to the invention will now be described with reference to the flowchart of FIG. 1.

The method comprises a first step 100 of constructing one knowledgebase and one classifying model per group from a set of learning spectra of microorganisms identified as belonging to said group. Generally, this step may be carried out in multiple ways with the aim of obtaining, for one or more given groups, a knowledgebase and a classifying model making it possible to determine whether a mass spectrum of an unknown microorganism belongs to said group on the basis of the list of peaks of the acquired spectrum. Excepting step 110, which is described below and implemented by a spectrometer, step 100 is implemented computationally, e.g. by means of one or more personal computers, servers, printed circuit boards, digital signal processors (or DSPs), and generally any microprocessor-based system able to receive data, store them, process them and produce as output processed data, for example for storage in a computer memory and/or for display on a screen, the system possibly itself comprising one or more microprocessor-based units in charge of processing specific data and communicating in them.

Figure 2:
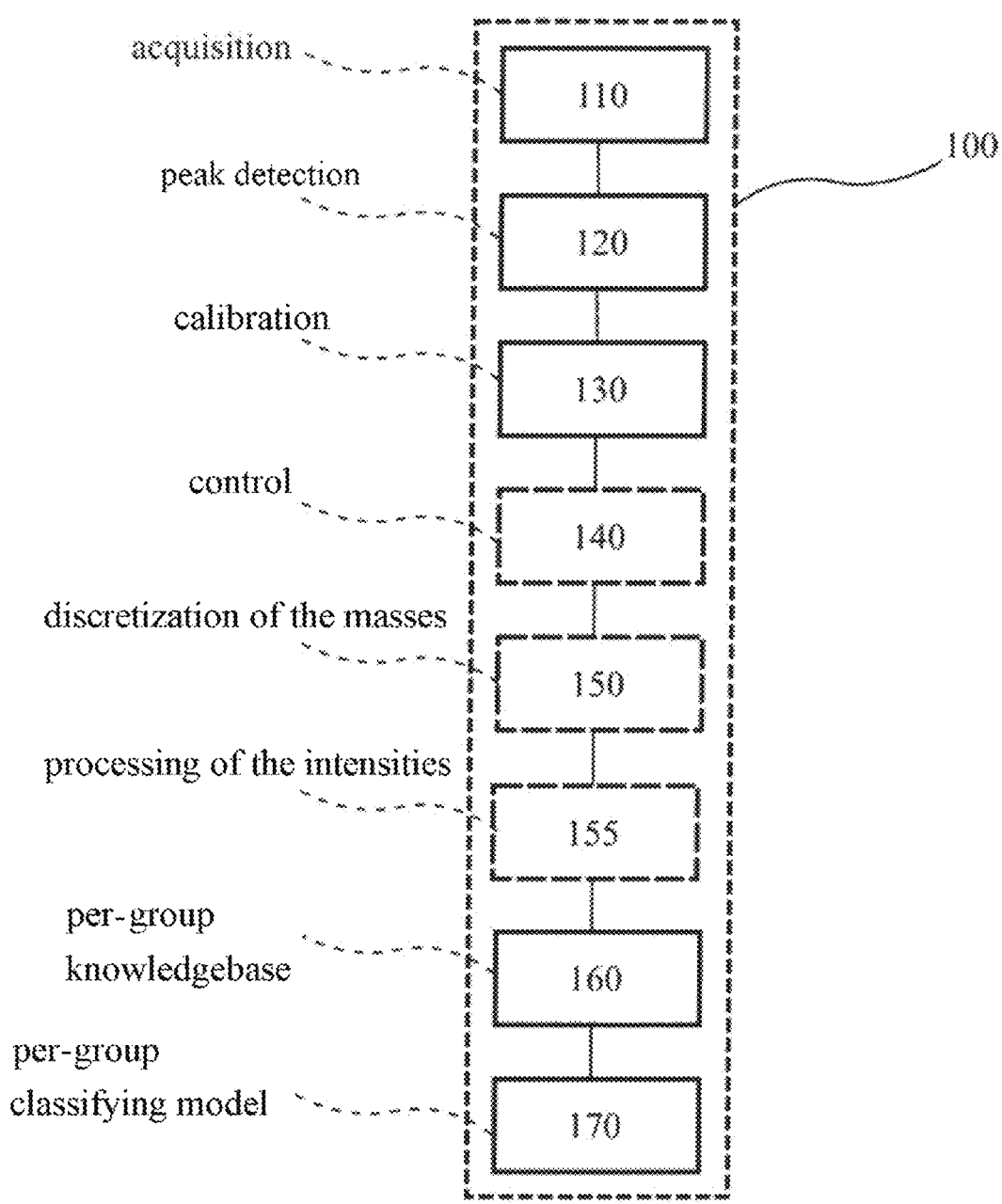
FIG. 2 is a flowchart of step 100 of the method according to the invention.

An example of an embodiment of this first step 100 is detailed in FIG. 2. The step 100 may thus start with a step 110 of acquiring a set of learning mass spectra of one or more microorganisms identified as belonging to a group, and an external-calibration mass spectrum, by means of MALDI-TOF (acronym for Matrix-assisted laser desorption/ionization time-of-flight) mass spectrometry. MALDI-TOF mass spectrometry is well known per se and will therefore not be described in more detail below. The reader may for example refer to the document Jackson O. Lay, "*Maldi-tof spectrometry of bacteria*", Mass Spectrometry Reviews, 2001, 20, 172-194. The acquired spectra are then preprocessed, in order in particular to denoise them, smooth them or even remove their baseline if necessary, in a way known per se.

The acquisition of a mass spectrum may consist in irradiating several times, with the laser, the sample in question in one or various positions of the sample on the holder. The obtained spectrum then consists of a "synthetic" spectrum obtained by summing, calculating a mean, calculating a median or any other method aiming to weight the contribution of the intensities of each spectrum of each of the irradiations to form the "synthetic" spectrum. This accumulation of irradiations, well known per se, in particular allows the signal-to-noise ratio to be increased while limiting the influence of non-repeatable effects due to the sample, the apparatus, to the conditions under which the acquisition is performed, etc.

A step of detecting the peaks present in the acquired spectra is then carried out in 120, for example by means of a peak-detecting algorithm based on the detection of local maxima. A list of peaks is thus produced for each acquired spectrum, said list including the location (also called the mass-to-charge value) and the intensity of the peaks of the spectrum.

Advantageously, the peaks are detected in a preset range $[m_{min}; m_{max}]$ thomson (Th) and preferably the range $[m_{min}; m_{max}]=[3000; 17000]$ thomson. Specifically, it has been observed that enough information is contained in this range of mass-to-charge ratios to identify microorganisms, and there is therefore no need to take into account a larger range.

The method continues, in 130, with a step of external calibration on the basis of the acquired calibration mass spectrum. This external calibration consists in adjusting the m/z axis of the mass spectra of a reference sample the content of which is known, so that the observed peaks coincide with their theoretical positions. An *Escherichia-coli* strain may for example serve as external standard for detecting the deviations and correcting the offsets in masses-to-charges. A list of reference peaks corresponding to characteristic masses-to-charges will have been defined beforehand for this calibrator. In this calibration step, the presence of the reference peaks corresponding to these characteristic masses-to-charges is sought in the list of peaks of the spectrum, with a given tolerance in the expected position. The spectrum is then realigned depending on the observed position. The transformation used to realign the acquired calibrator peaks with the reference peaks will then be used to realign the peaks of the spectrum of the sample.

According to one example of implementation of this step 130, for each acquisition group (for example 4×4 locations on an acquisition holder for a VITEK® MS apparatus as sold by the applicant) a calibration *Escherichia-coli* strain (ATCC 8739) is deposited in the location reserved for the calibration of said acquisition group. Once the spectrum of the calibration strain has been acquired, the presence of 11 reference peaks corresponding to characteristic masses-to-charges of *Escherichia coli* is sought, with a tolerance of 0.07% around the expected position of the peaks. If at least 8 peaks from the 11 are found in the expected position interval, the peaks of the spectrum of the calibration strain will be realigned to reflect their reference position. The transformation used to realign the acquired calibrator peaks with the reference peaks, for example a polynomial transformation of first or second order, will then be used to realign the peaks of the spectra of all the other locations of the acquisition group.

Optionally and by way of precaution, the acquisition operation may be stopped if a minimum number of detected reference peaks is not reached, for example if fewer than 8 characteristic masses-to-charges are detected. It is also possible to increase the tolerance around the positions of the expected reference peaks to 0.15%. In this case, if at least 5 characteristic masses-to-charges are detected with the new increased tolerance, it is preferable to firstly realign the peaks of the calibrator spectrum and then to seek a larger number of reference peaks with the initial tolerance of 0.07%. If a larger number of peaks is then found, the peaks of the spectrum are realigned a second time using the determined transformation.

The acquisition, the preprocessing and the detection of the peaks of the other samples composing the acquisition group may also be carried out after the calibration step, the determined transformation being applied to the lists of peaks corresponding to the spectra of the samples. Alternatively, step 130 may consist of or be complemented by a step of internal adjustment on the basis of a calibrator mixed with the sample in the acquiring step 110.

Following the calibration step 130, the method according to the invention may comprise a step 140 of controlling the quality of the acquired spectra and/or a step 150 of discretizing the masses-to-charges and/or a step 155 of processing the intensity of the spectra. The order in which these steps 140, 150, 155 are carried out may vary.

Optionally, the method therefore continues, in 140, with a step of controlling the quality of the acquired spectra. For example, it may be checked that the number of identified peaks is sufficient, too low a number of peaks not allowing the acquired spectrum to be used to classify the microorganism in question whereas too high a number may be a sign of noise. In addition, a test based on the intensity of the detected peaks may also be carried out in this step of controlling the quality of the spectra.

Following step 130 and optionally step 140, a step 150 of discretizing the masses-to-charges, or of binning the masses-to-charges may be carried out. To do this, the $[m_{min}; m_{max}]$ thomson range is subdivided into width intervals or bins the width of which is for example constant or constant on a logarithmic scale. For each interval comprising a plurality of peaks, a single peak may be kept, advantageously the peak having the highest intensity. This method is therefore used to align the spectra and to decrease the effects of slight errors in the position of the masses-to-charges, the obtained alignment being directly related to the size of the discretization intervals. A shorter list is thus produced from each of the lists of peaks of the measured spectra. Each component of the list corresponds to an interval of the discretization and has for value the intensity of the peak kept for this interval, the value "0" meaning that no peak was detected in this interval.

Following step 130, optionally step 140 and optionally step 150, a step 155 of processing the intensity of the spectra may also be carried out. Intensity is a quantity that varies greatly from one spectrum to the next and/or from one spectrometer to the next. Because of this variability, it is difficult to use raw intensity values in classifying tools. This step may therefore be carried out on the raw spectra, before discretization of the masses-to-charges or after step 150. This step may in particular consist of a step of thresholding the intensities, intensities lower than the threshold being considered to be zero and intensities higher than the threshold being kept. As a variant, the lists of intensities obtained via this thresholding or following a discretizing step may be "binarized" by setting the value of a component of the list to "1" when a peak is higher than the threshold or present in the corresponding discretization interval, and to "0" when a peak is lower than the threshold or when no peak is present in this discretization interval. Alternatively, the lists of intensities obtained are transformed according to a logarithmic scale, the value of the component being set to "0" when no peak is present in the interval or when a peak is lower than the threshold. Lastly, each of the lists of intensities (which are either raw, thresholded, "binarized" or transformed according to a logarithmic scale) may be normalized.

Advantageously, the lists of intensities are transformed according to a logarithmic scale then normalized. This has the effect of making the learning of the classifying algorithms, which occurs subsequently, more robust.

From these lists of peaks, each of which corresponds to a learning spectrum of a microorganism identified as belonging to a group, the method continues with the creation, in step 160, of one knowledgebase per group, and, in step 170, of one classifying model per group. The knowledgebase contains the parameters of the classifying model and information on the groups of each microorganism used for the learning and allows an unknown microorganism to be classified among the groups of the learning microorganisms.

One classifying model is established per group in the step 170 on the basis of known supervised classifying algorithms such as the nearest neighbor method, logistic regression, discriminant analysis, classification trees, regression methods of the "LASSO" or "elastic net" type, SVM algorithms (SVM standing for "support vector machine").

Figure 1:
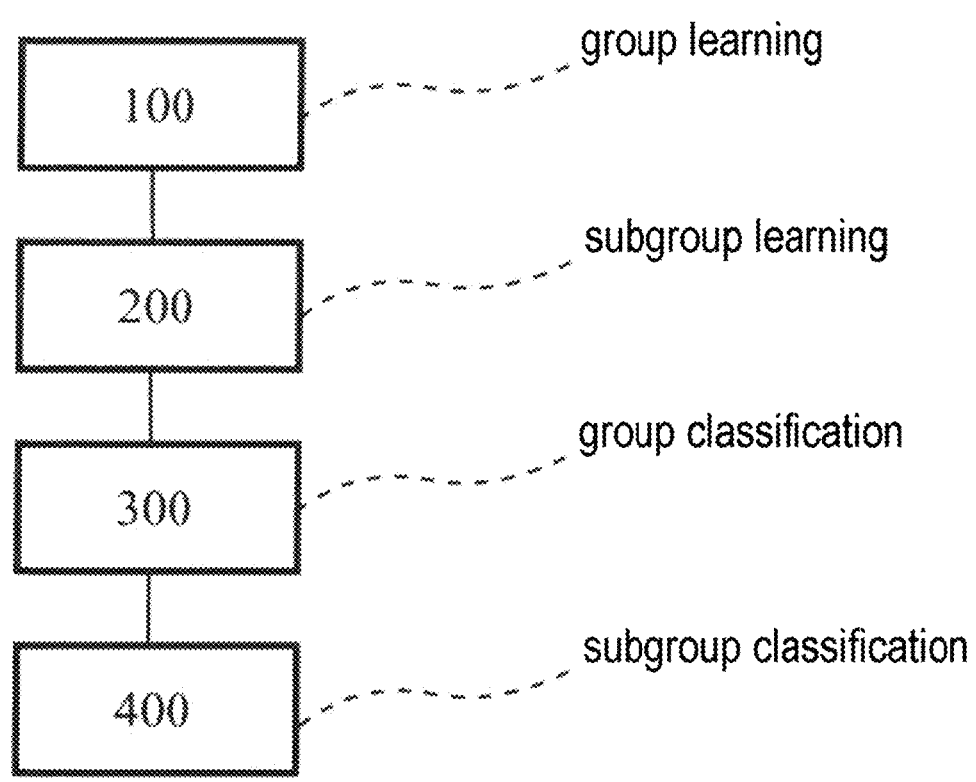
FIG. 1 is a flowchart of the method according to the invention.

In FIG. 1, the method continues, in step 200, with the construction of one knowledgebase and one classifying model per subgroup on the basis of a set of learning spectra of microorganisms identified as belonging to the preceding group and to subgroups of this group. Excepting step 210, which is described below and implemented by a spectrometer, step 200 is implemented computationally, e.g. by means of one or more personal computers, servers, printed circuit boards, digital signal processors (or DSPs), and generally any microprocessor-based system able to receive data, store them, process them and produce as output processed data, for example for storage in a computer memory and/or for display on a screen, the system possibly itself comprising one or more microprocessor-based units in charge of processing specific data and communicating in them.

Figure 3A:
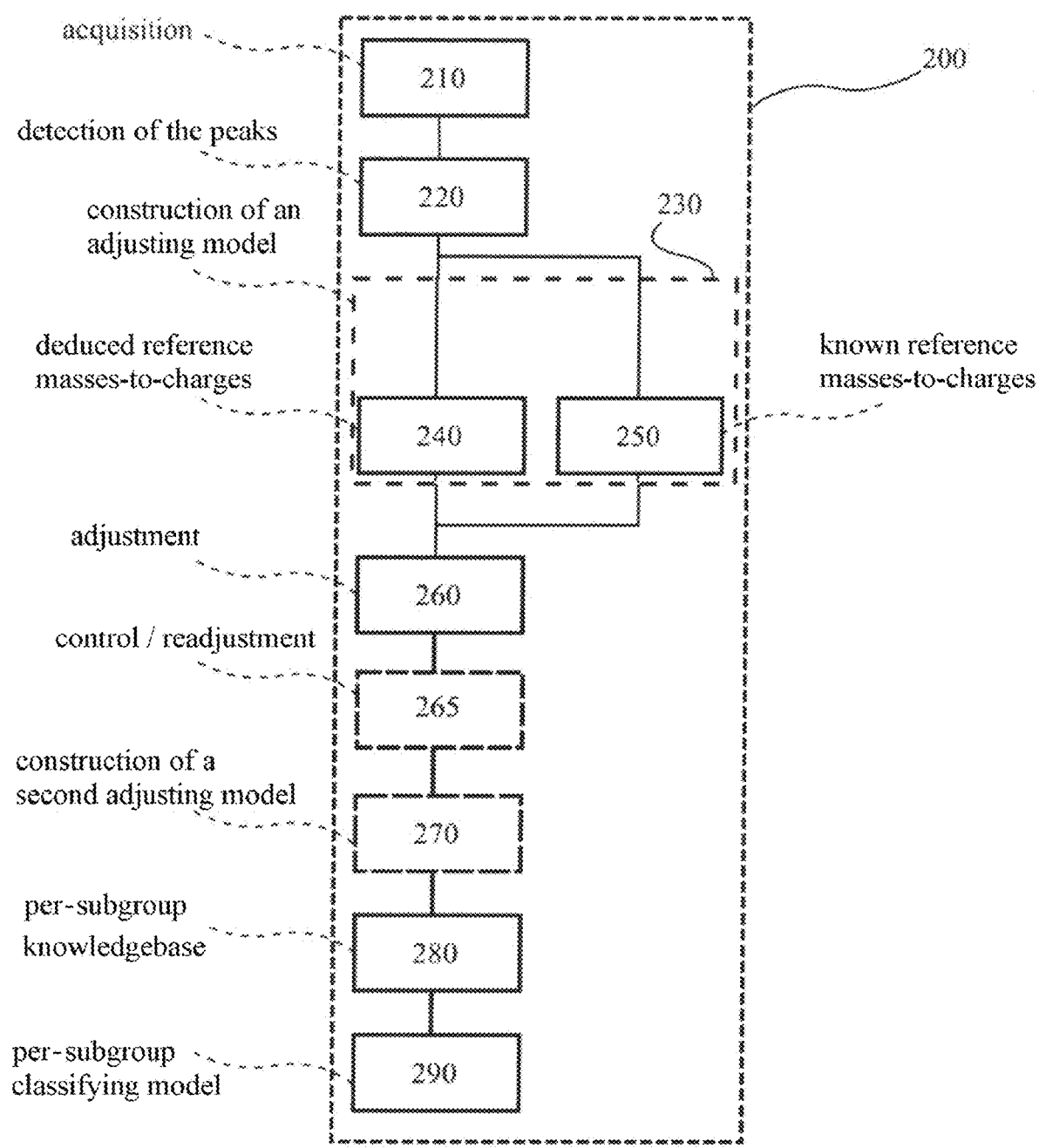
FIG. 3a is a flowchart of step 200 of the method according to the invention.

Step 200 is detailed in FIG. 3a. This step 200 comprises acquiring 210 at least one spectrum of a microorganism the group and subgroup of which are known and doing so for each of said subgroups. This acquiring step is carried out in a similar way to step 110. The acquired spectrum is thus preprocessed, in order in particular to denoise it, smooth it or even remove its baseline if necessary. The method continues in step 220 with the identification of the peaks of the spectra in a similar way to step 120, the internal or external calibration of each of the spectra in a similar way to step 130, and optionally the control of their quality in a similar way to step 140.

Preferably, step 210 may be directly carried out simultaneously with step 110 of the method in order to limit the number of manual steps necessary in the acquiring steps. Steps 110 and 210 then consist of a single step of acquiring a spectrum of a microorganism the group and subgroup of which are known. In the same way, step 220 is then carried out simultaneously with steps 120 and 130 and optionally step 140.

Following step 220, the spectra of the microorganisms the group and subgroups of which are known are then represented in the form of a set of lists of peaks, each list of peaks corresponding to one microorganism the group and subgroup of which are known.

On the basis of these lists of peaks, the method continues with a step 230 of constructing an adjusting model allowing mass-to-charge offsets of the acquired spectra to be corrected. This constructing step 230 firstly includes a step of identifying and selecting reference masses-to-charges that are common to the various subgroups. Specifically, a mass-to-charge that was not common to the various subgroups of the group would be a discriminant mass-to-charge, and an adjusting model based on this mass-to-charge would therefore be biased. Ideally, these masses-to-charges are common to the various subgroups and contain no peaks in immediate proximity in the spectrum in order to obtain a list of masses-to-charges that particularly characterizes the group.

According to a first alternative 240, these reference masses-to-charges that are common to the various subgroups are deduced from statistical criteria.

Figure 3B:
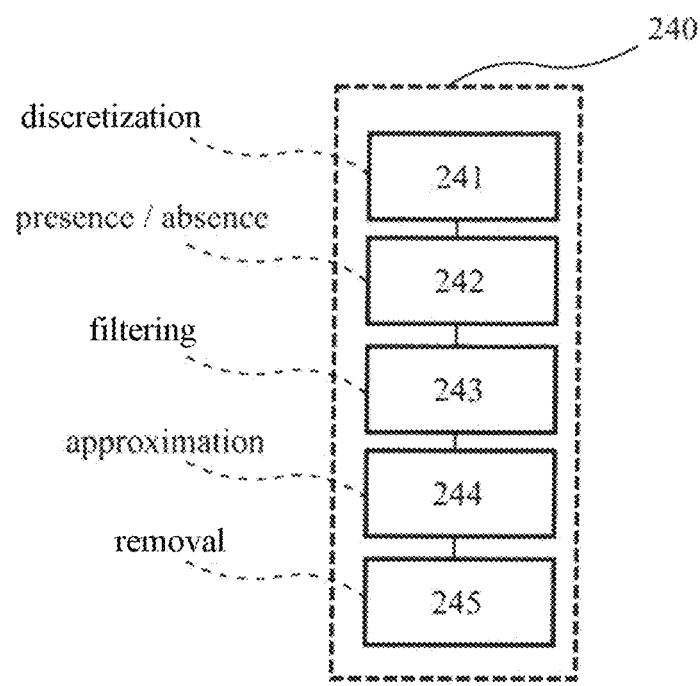
FIG. 3b is a flowchart of step 240 of the method according to the invention.

As illustrated in FIG. 3b, these reference masses-to-charges may in particular be obtained by:
a first step 241 of discretizing the range of masses-to-charges of interest.

This step may be carried out over a mass-to-charge interval of the lists of peaks that is restricted with respect to the mass-to-charge interval obtained following the acquisition, which interval is known to contain most of the characteristic masses-to-charges of the microorganisms, for example over the mass-to-charge range extending from 3000 to 17000 Th. On the basis of this interval, the latter is discretized:
either into mass-to-charge intervals that are regular (for example 1 Th)
or into increasing mass-to-charge intervals.
Thus a set $$\{m(i)\}; i=1,\ldots,I$$

is obtained corresponding to all the masses-to-charges obtained after discretization, each value m(i) being separated from the value m(i+1) by a mass-to-charge interval called the discretization pitch.

A tolerance factor $t_1$ defining an interval around each of the masses-to-charges m(i) is defined. For the method to work as it should it will be noted that the chosen discretization must at least guarantee the overlap of the intervals defined by the tolerance factor $t_1$ from one mass-to-charge to the following, ideally an overlap of half the width of the interval. Thus, a small discretization pitch is preferable to too large a discretization pitch in order not to discard a mass-to-charge that is characteristic of the subgroups and that would therefore be useful for the adjustment. A small discretization pitch therefore allows the loss of information to be limited.

One way of guaranteeing the overlap of the intervals from one mass-to-charge to the following is to define the discretization iteratively with the formula $$m(i+1)=m(i)+t_1*m(i)$$

where $t_1$ is the tolerance factor, and to initialize m(1) at the minimum limit of the range of masses-to-charges of interest. The discretization pitch is thus equal to $t_1*m(i)$. For example, for the range of masses-to-charges of interest of 3000 to 17000 Th with a tolerance of $t_1=0.0008$, the discretization pitch at 3000 Th is 2.4 Th whereas the discretization pitch at 17000 Th is 13.6 Th.

Another, simpler, way of guaranteeing the overlap of the intervals from one mass-to-charge to the following is to define the discretization at the minimum limit of the range of masses-to-charges of interest with the formula $$m(i+1)=m(i)+t_1*m(1)$$

For example, for the mass-to-charge range of interest of 3000 to 17000 Th with a tolerance $t_1=0.0008$, the discretization pitch applicable to all the mass-to-charge range is 3000*0.0008=2.4 Th.

There follows a second step 242 of detecting the presence or absence of one or more peaks in the interval according to $t_1$ around each mass-to-charge m(i) defined by the discretizing step. For each spectrum, the tolerance $t_1$ allows uncertainty in the position of the mass-to-charge sought in each of the acquired spectra to be taken into account.

Thus the list of the masses-to-charges of the spectrum in question is $$X=\{x(s)\}; s=1,\ldots,S$$

and the tolerance factor applied to the masses-to-charges is $t_1$. The operation consists in seeking the presence of a peak among $X=\{x(s)\}; s=1,\ldots,S$ in the interval defined by the tolerance around the mass-to-charge m(i) in question, namely the interval $[m(i)-m(i)*t_1; m(i)+m(i)*t_1]$ In order to optimize computation time, the presence of a peak in the interval in question may be denoted 1 and the absence of a peak or the presence of a plurality of peaks denoted 0, in order to obtain a presence matrix taking the form of table 1 below, T being the number of learning spectra acquired:

TABLE 1

|  | Subgroup | m(1) | m(2) | ... | m(I-1) | m(I) |
|---|---|---|---|---|---|---|
| Spectrum(1) | A | 0 | 0 |  | 1 | 1 |
| Spectrum(2) | A | 0 | 0 |  | 1 | 1 |
| ... |  |  |  |  |  |  |
| Spectrum(T-1) | B | 0 | 1 |  | 1 | 1 |
| Spectrum(T) | B | 1 | 1 |  | 1 | 1 |

On the basis of this matrix, a third step 243 consists in filtering the masses-to-charges depending on the frequency of presence of peaks per subgroup.

The frequency of presence of a peak in the interval defined by the tolerance around each mass-to-charge m(i), i.e. the tolerance defined during the discretization step, is calculated per subgroup and converted into a percentage.

Figure 4:
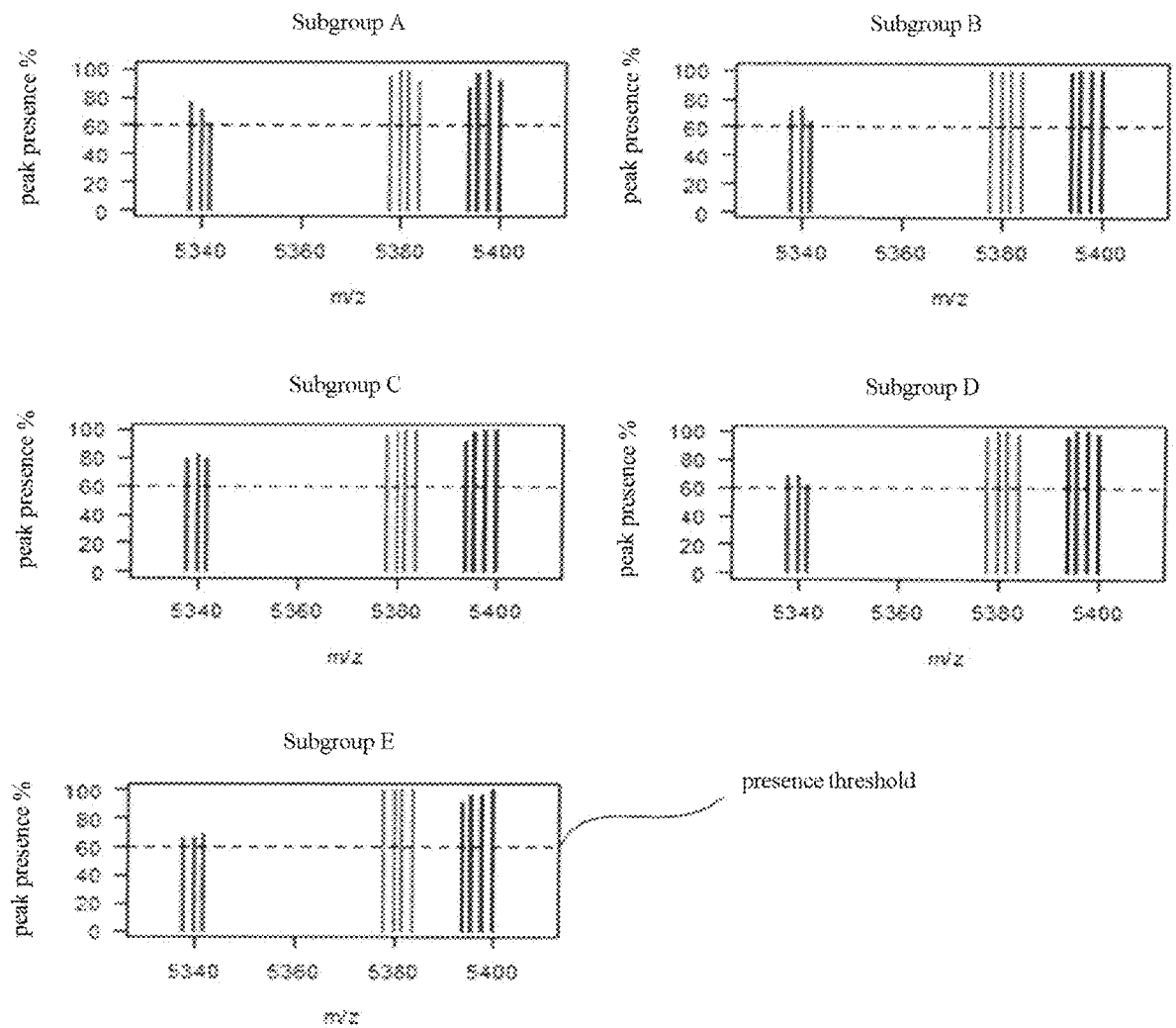
FIG. 4 is a chart for each subgroup A to E, of a given group, of the frequency of each peak, said peaks being obtained from the spectra corresponding to said subgroup in the interval 5330 Th-5410 Th

This step is illustrated in FIG. 4. FIG. 4 shows, for each subgroup A to E, of the group in question, the frequency of each peak, these peaks being obtained from the spectra corresponding to said subgroup in the interval 5330 Th-5410 Th.

Below, the masses-to-charges m(i) having, for each of the subgroups to be discriminated, a presence percentage higher than a threshold, for example 60%, which threshold is represented by a dashed horizontal line in FIG. 4, are retained.

Thus among:

$\{m(i)\}; i=1, \ldots, I$, a set of masses-to-charges
$\{m(j)\}; j=1, \ldots, J; J \leq I$ is obtained, these masses-to-charges being retained after the step of filtering with respect to frequency. For example, according to table 2 below, only the masses-to-charges m(I-1) and m(I) are retained after filtering.

TABLE 2

| Frequency (%) per subgroup | m(1) | m(2) | ... | m(I-1) | m(I) |
|---|---|---|---|---|---|
| A | 0 | 0 | | 100 | 100 |
| B | 50 | 100 | | 100 | 100 |

On the basis of this list of masses-to-charges filtered according to a frequency threshold, the following step 244 consists in approximating the position of said retained masses-to-charges.

The retained masses-to-charges have a ballpark precision depending on the discretization carried out in step 241. A step of approximating the position of these masses-to-charges is thus carried out in order to obtain a position representative of the distribution of the positions of the peaks present around the mass-to-charge m(j). This computation of representative position may for example comprise a step of estimating a Gaussian function representative of the distribution of the peaks and of seeking the position of the extremum of this function. Another method may consist in performing a plurality of steps of iteratively computing the median value of the positions of the peaks present around the mass-to-charge m(j). For this method using the median, M(j) is the theoretical value of the position of the mass-to-charge. If $M(j, 0)=m(j)$, $M(j, n+1)$ is obtained with the following algorithm:

For each spectrum, one step of the method consists in seeking a peak among $X=\{x(s)\}; s=1, \ldots, S$ present in the interval around the mass-to-charge $M(j, n)$, namely the interval $[M(j,n)-M(j,n)*t_2; M(j,n)+M(j,n)*t_2]$ where $t_2$ is a tolerance factor around the position of the mass-to-charge $M(j,n)$, the value of the tolerance factor $t_1$ being higher than or equal to $t_2$.

The value of $M(j, n+1)$ is then obtained by calculating the median of the values of the retained peaks over all of the spectra in the interval around $M(j,n)$.

The criterion for stopping this optimizing step may for example be a predefined number of iterations and/or be based on an inspection of the increment.

For example, in the case where a predefined number of iterations is defined:

if N is the predefined number of iterations, M(j) is approximated by $\hat{M}(j)=M(j,N)$.

In the case where the method comprises a step of inspecting the increment, let ε be a tolerance set for the refined computation of M(j). The iterations end once:

$|M(j,n+1)-M(j,n)|\varepsilon$

M(j) is then approximated by $\hat{M}(j)=M(j, n+1)$.

In order to ensure the convergence of this method via inspection of the increment and to save on the computing time required for this step, a maximum number N of iterations may also be defined beforehand.

Figure 5A:
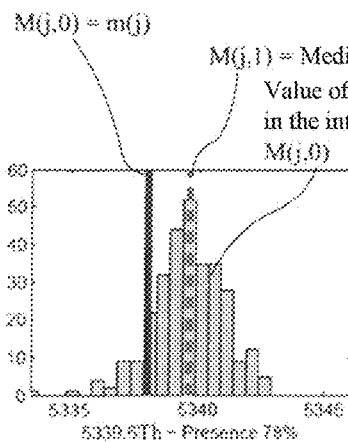
FIGS. 5a to 5i are a chart of an example of iterative computation in three iterations of three approximate masses-to-charges
Figure 5B:
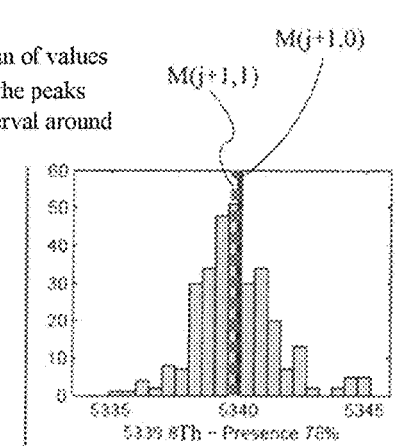
Figure 5C:
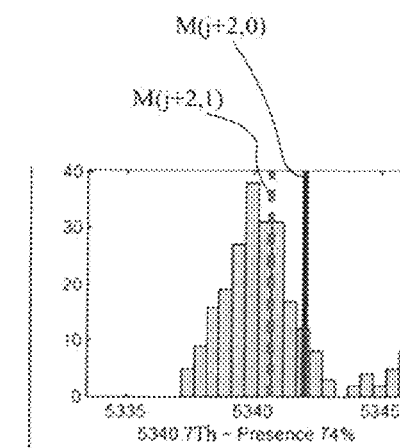
Figure 5D:
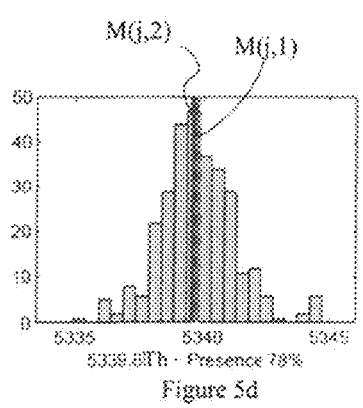
Figure 5E:
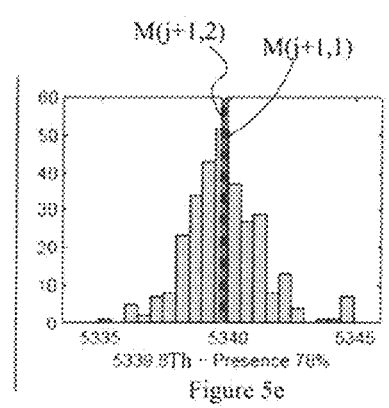
Figure 5F:
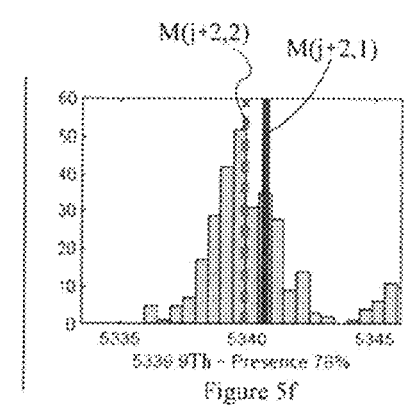
Figure 5G:
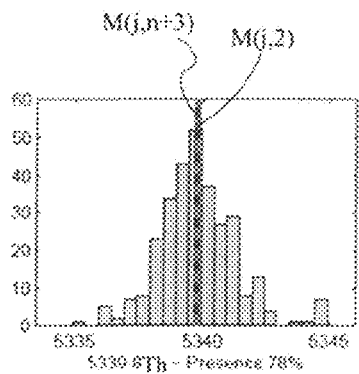

The stopping criteria based on a predefined number of iterations N=3 is thus preferred for the implementation of the invention. An example of an iterative computation in three iterations is illustrated for three masses-to-charges in FIGS. 5a to 5i. In FIG. 5a, the median M(j, 1) calculated on the basis of values of the peaks around M(j, 0) is equal to 5339.6 Th and represented by a dashed vertical line. In a second iteration, illustrated in FIG. 5d, the median M(j, 2) is thus calculated on the basis of the values of the peaks around M(j, 1), and a new value equal to 5339.8 Th is then obtained. In FIG. 5d, M(j, 1) is represented by a solid vertical line and M(j, 2) is represented by a dashed vertical line. In a third iteration, illustrated in FIG. 5g, the median M(j, 3) is thus calculated on the basis of the values of the peaks around M(j, 2), and a value equal to 5339.8 Th is then obtained again, demonstrating the convergence of the method. In FIG. 5g M(j, 2) is represented by a solid vertical line and M(j, 3) is represented by a dashed vertical line. The computation is stopped on this third iteration and the approximate value of 5339.8 Th is kept for the mass-to-charge retained by the discretization of 5338 Th.

Figure 5H:
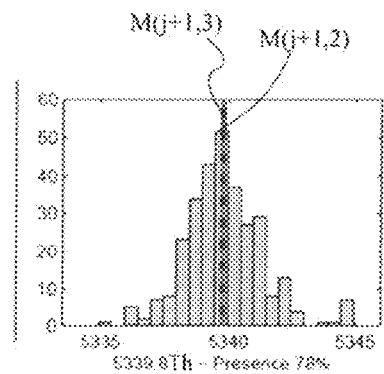
Figure 5I:
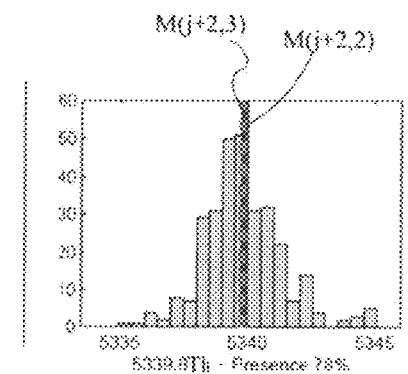

A computation in three similar steps is carried out for each of the theoretical masses-to-charges obtained following the discretization. Thus, FIGS. 5b, 5e and 5h illustrate a convergence of the mass-to-charge retained by the discretization $M(j+1, 0)=m(j+1)$ from a value of 5340 Th to an approximate value of M(j+1,3) of 5339.8 Th. Likewise, FIGS. 5c, 5f and 5i illustrate a convergence of the mass-to-charge retained by the discretization $M(j+2,0)=m(j+2)$ from a value of 5342 Th to an approximate value of M(j+2, 3) of 5339.8 Th.

Following the approximating step 244, the method continues with a step 245 of removing identical approximate masses-to-charges.

Following the approximation, a list $\{m(j), \hat{M}(j)\}, j=1, \ldots, J$ is obtained. Because the initial discretization was chosen so as to guarantee an overlap of the intervals from one mass-to-charge to the following, a plurality of retained masses-to-charges m(j) may correspond to the same approximate mass-to-charge. The approximations $\hat{M}(j)$ of these masses-to-charges are in this case equal or almost equal depending on the precision retained in the computation of the value. Table 3 below in particular illustrates the position of the retained approximate masses-to-charges in the interval 5338 to 5398 Th for an example of an implementation of the invention with a discretization pitch of 2 Th.

TABLE 3

| Position of the masses-to-charges m(j) | Approximate position of the masses-to-charges $\hat{M}(j)$ | Kept approximate position of the masses-to-charges $\hat{M}(j)$ |
|---|---|---|
| 5338 | 5339.8 | 5339.8 |
| 5340 | 5339.8 | |
| 5342 | 5339.8 | |
| 5378 | 5381.2 | 5381.2 |
| 5380 | 5381.2 | |
| 5382 | 5381.2 | |
| 5384 | 5381.2 | |
| 5394 | 5397.4 | 5397.4 |
| 5396 | 5397.4 | |
| 5398 | 5397.4 | |

A single approximation is thus kept for each value.

A new list $R=\{R(k)\}$; $k=1, \ldots, K$; $K \leq J$ of the reference masses-to-charges of the group is thus obtained.

According to a second alternative 250, these masses-to-charges that are common to the various subgroups are known beforehand. They may for example be determined on the basis of the list of the peaks used as reference peaks for the group-level classification. Since these peaks are known to represent the group, there is a high probability that they will be able to be used as reference masses-to-charges in the context of the present invention. These masses-to-charges may also be known from prior analyses by mass spectrometry or by other analytical methods that allow the theoretical mass-to-charge of a peak to be determined for a molecule or protein that is characteristic of the various subgroups, and therefore of the group in question.

Optionally, and with the objective of improving the selection of these masses-to-charges, a step that is similar to the step 242 of detecting the presence or absence of one or more peaks in a tolerance interval around each already known reference mass-to-charge may be carried out. This step 242 may be followed by a step that is similar to step 243 consisting in filtering the masses-to-charges depending on the frequency of presence of peaks per subgroup may be carried out.

The frequency of presence of a peak in the interval defined by the tolerance around each already known reference mass-to-charge is calculated per subgroup and converted to a percentage.

Alternatively or in addition, this step 242 may be followed by a step that is similar to the step 244 of approximating the position of the already known reference masses-to-charges may be carried out.

Once the list of reference masses-to-charges obtained following step 240 or 250, the method continues with the adjustment of the masses-to-charges of all of the lists of peaks in step 260 according to FIG. 3a.

For each spectrum represented by a list of peaks, the objective of step 260 is to adjust the positions of all the peaks by learning a transforming model on the basis of the position of the reference masses-to-charges. The parameters of this model are estimated so that the peaks observed in the spectrum coincide as well as possible with the approximate position of the reference masses-to-charges obtained at the end of step 240 or with the theoretical position of the reference masses-to-charges obtained at the end of step 250.

For each spectrum in the list-of-peaks format:

$X=\{x(s)\}$; $s=1, \ldots, S$ is the list of the masses-to-charges of the peaks of the spectrum in question $R=\{R(k)\}$; $k=1, \ldots, K$ is the list of the reference masses-to-charges $t_3$ is the tolerance factor around the position of the mass-to-charge $\{R(k)\}$, for example $t_3=0.0004$. The value of the tolerance factor $t_2$ is higher than or equal to $t_3$ For each reference mass-to-charge $\{R(k)\}$, the method consists in seeking a mass-to-charge among $\{x(s)\}$, $s=1, \ldots, S$ present in the interval defined by the tolerance around the mass-to-charge $\{R(k)\}$, namely the interval $$[R(k)-R(k)*t_3;R(k)+R(k)*t_3]$$

In certain cases, when the offset of the masses-to-charges of the spectrum is too large or for example when the spectra contain only few peaks, no peak is observed in the interval in question.

The sequence of observations $\{R(l); x(l)\}$, $l \subseteq \{1, \ldots, K\}$ is the list of the reference masses-to-charges $\{R(l)\}$ for which a peak in position $x(l)$ in the spectrum in question has been observed. The transformation to be applied to the masses-to-charges of the spectrum is modelled with the model $R=f(x)$, the model f possibly being:

a linear-regression model:
$C=\beta_0+\beta_1 x$; $\beta_0$ and $\beta_1$ being the constants of the model a 2nd-order polynomial-regression model:
$C=\beta_0+\beta_1 x+\beta_2 x^2$; $\beta_0$, $\beta_1$ and $\beta_2$ being the constants of the model a non-parametric or non-linear regression model, for instance local regression models such as regressions of the spline, Loess or Lowess type or kernel-regression models, etc.

A linear-regression model is preferred for the implementation of the invention in order to limit prediction error when the model is extrapolated out of the mass-to-charge domain used to estimate the parameters of said model. The need to extrapolate arises for example when the selected reference masses-to-charges cover only a subset of the mass-to-charge domain of interest or when the offset of the masses-to-charges of the spectrum in question is too large relative to the tolerance $t_3$ in question.

The parameters of the model may be estimated with the ordinary least-squares method. However, aberrant values may be observed for certain masses-to-charges, due for example to the specificity of the tested sample or to an initial offset of the masses-to-charges that is too large in a certain zone of the mass-to-charge range. The least-squares method is very sensitive to the presence of aberrant values, even if they are small in number. In order to obtain parameter estimations that are not influenced by aberrant points, it is preferable to use what is called a robust estimating method that allows the problem of the detection of aberrant points and of the estimation of the parameters of the model to be solved simultaneously. Tukey's biweight estimator is thus preferred for the implementation of the invention, and preferably solved via the use of an iteratively reweighted least squares (IRLS) algorithm. Other robust estimating methods may obviously be envisioned, inter alia the least median of squares (LMS) method, the least trimmed squares (LTS) method and any method taken from the M-estimator class, of which Tukey's biweight estimator is one particular example.

The adjusted position of all the peaks of the spectrum is then inferred via the model learnt beforehand from the reference masses-to-charges. The correction of the masses-to-charges is thus extrapolated beyond the interval of the masses-to-charges used for the adjustment:

For each mass-to-charge $x(s)$, the adjusted mass-to-charge is obtained with $\hat{x}(s)=f(x(s))$ The list of the adjusted positions of the peaks of the spectrum is denoted $\hat{X}(s)=\{\hat{x}(s)\}$; $s=1, \ldots S$.

Following the adjusting step 260, an optional step 265 may consist in optimizing the list of reference masses-to-charges, this optimization being based on the quality of the obtained adjustment. The objective of this step is to ensure that the quality of each retained reference mass-to-charge is similar between the various subgroups of interest.

For each reference mass-to-charge $R=\{R(k)\}$; $k=1, \ldots, K$; $K \leq J$ and each subgroup:

The method comprises a step of computing the frequency of presence of a peak for each subgroup after adjustment of the masses-to-charges of each spectrum in the interval defined by the tolerance $t_3$ around the mass-to-charge $R(k)$. This frequency forms a first indicator.

Following this step, the method comprises a step of computing the discrepancy in the position of the peaks for each subgroup after adjustment to the reference mass-to-charge, for example by computing the median or the mean of residues associated with the mass-to-charge R(k). This discrepancy forms a second indicator.

There follows a step of computing the dispersion in the positions of the peaks for each subgroup after adjustment with respect to the reference mass-to-charge, for example by computation of a standard deviation, a range, or even an interquartile interval of residues associated with the mass-to-charge R(k). Generally, this step of computing dispersion may be carried out with any method allowing the dispersion of the values of the positions of the observed peaks to be quantified. This dispersion forms a third indicator.

On the basis of this computation, step 265 continues with a step of removing certain reference masses-to-charges based on the nonuniformity of at least one of the three indicators between the subgroups of the group in question.

Figure 6:
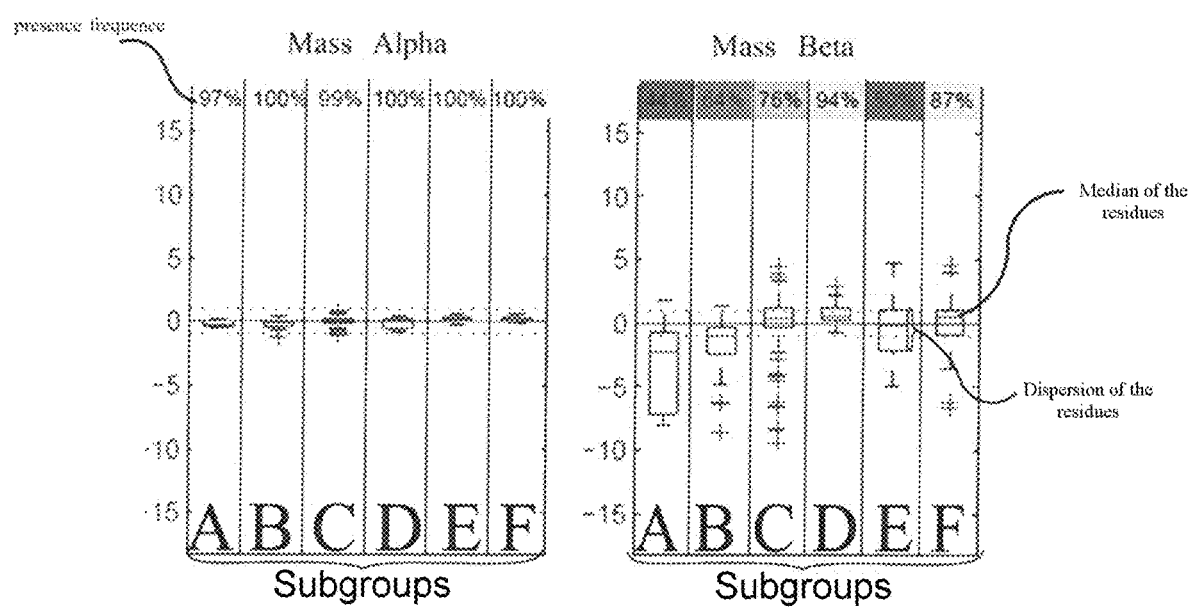
FIG. 6 is a chart for two masses-to-charges Alpha and Beta of the frequency of presence of a peak for each subgroup A to F, the median of the residues for each subgroup, and the interquartile interval of the residues for each subgroup

FIG. 6 illustrates for two masses-to-charges Alpha and Beta, the computation of:
the frequency of presence of a peak for each subgroup A to F
the median of the residues for each subgroup, which median is represented by a horizontal line in the interior of each box-and-whisker plot
the interquartile interval of the residues for each subgroup, which is represented by the extent of each box-and-whisker plot.

Thus, these three indicators for example allow the mass-to-charge Alpha to be kept and the mass-to-charge Beta to be discarded. Specifically, the mass-to-charge Alpha has a frequency of about 100% between the subgroups, a median of the residues that is close to 0 for each subgroup and a dispersion of the residues that is similar between each subgroup. In contrast, the mass-to-charge Beta should be excluded because the frequency of presence of a peak is lower than 60% for 2 subgroups, the median of the residues is beyond a threshold of 1 or −1 for the subgroup A, a median threshold being set to 1 or −1 (dashed line). In addition, the interquartile interval of the residues is clearly higher for the subgroups A and E. The computation of these three criteria therefore allows thresholds allowing masses-to-charges to be statistically discarded or kept to be established.

Step 265 then ends with a readjusting step that is similar to step 260 but carried out only on the basis of the masses-to-charges retained after the step of removing certain reference masses-to-charges based on the nonuniformity of at least one of the three indicators between the subgroups of the group in question.

Optionally, step 260 or step 265 may be followed by a step 270 of learning and constructing a second model allowing the masses-to-charges to be adjusted in the mass-to-charge range of interest for the per-subgroup classification.

The step 270 repeats step 230 of identifying and selecting reference masses-to-charges that are common to the various subgroups and step 260 of learning and constructing a model for adjusting the masses-to-charges in order to construct a second adjusting model on the basis of the lists of peaks having already undergone a first adjustment, and therefore with mass-to-charge offsets that are assumed to be smaller.

Specifically, the first adjusting step, following step 260, may lead to an extrapolation of the reset of the masses-to-charges in certain zones of the range of masses-to-charges of interest following a substantial initial offset of the masses-to-charges. A second step of learning and constructing a second model allowing the masses-to-charges to be adjusted via a polynomial-regression model, for example of the 2nd order, may be carried out in order to more finely adjust the position of the peaks in a larger range of masses-to-charges. To do this, steps 230, and 260, and even 265, are reproduced in order to select a list of reference masses-to-charges that are common to the various subgroups and to adjust the masses-to-charges of all of the lists of peaks over the mass-to-charge range of interest for the per-subgroup classification.

Figure 7A:
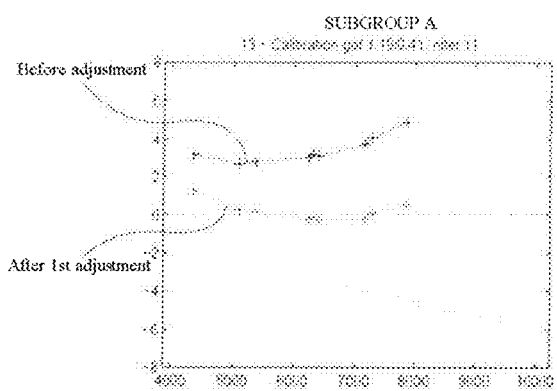
FIGS. 7a and 7b are a chart of the result of a first adjustment and a second adjustment according to the invention
Figure 7B:
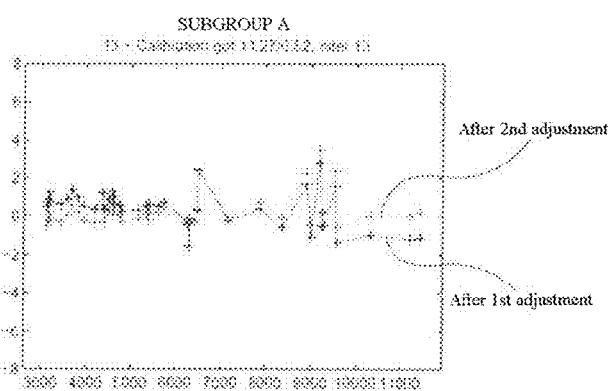

FIGS. 7a and 7b illustrate the advantage of this second adjusting step.

FIG. 7a illustrates the result of a first adjustment via a linear-regression model for a spectrum of a given subgroup A. The black curve represents the discrepancy between the reference mass-to-charge and the position of the mass-to-charge observed before adjustment. The gray curve for its part represents the discrepancy between the reference mass-to-charge and the position of the mass-to-charge after adjustment. Because of a high initial offset of the masses-to-charges, only the reference masses-to-charges between 4000 Th and 8000 Th have been detected. The model for correcting the masses-to-charges is then extrapolated out of this interval of masses-to-charges over all of the peaks of the spectrum in question. The use initially of a linear model allows the extrapolation error to be limited.

FIG. 7b illustrates the result of a second adjustment of the same spectrum via a 2nd-order polynomial-regression model. The black curve represents the discrepancy between the reference mass-to-charge and the position of the mass-to-charge observed after the first adjustment, but before the second adjustment. The gray curve represents for its part the discrepancy between the reference mass-to-charge and the position of the mass-to-charge after the second adjustment. It will be noted that the model has been adjusted for the masses-to-charges detected between 3000 Th and 12000 Th, allowing the position of the peaks to be more finely adjusted over a wider range of masses-to-charges.

Step 270 may optionally be repeated n times in order to construct an n-th adjusting model and thus improve the adjustment of the spectra.

The following step 280 lastly consists in learning and constructing a dedicated knowledgebase and, in the following step 290, a dedicated classifying algorithm allowing subgroups to be discriminated on the basis of the lists of peaks of spectra having undergone the adjustment or the steps of adjusting the masses-to-charges described above.

The one or more steps of adjusting the masses-to-charges having allowed the precision of the location of the peaks to be significantly improved, the classifying algorithm may be:
based on the computation of a tolerance distance, for example equal to or advantageously smaller than that for a group-level classification,
based on a matrix of peaks, for example obtained by discretization of the masses-to-charges such as described in step 150. The pitch used for the discretization of the masses-to-charges being identical or advantageously finer than for a group-level classification.

Any known classification algorithm (such as logistic regression, discriminant analysis, classification trees, regression methods of the "LASSO" or "elastic net" type, or algorithms of the SVM type (SVM standing for "support vector machine"), may be used.

The method according to the invention therefore allows a model for adjusting the masses-to-charges comprising 1 to n lists of reference masses-to-charges and 1 to n models for adjusting the masses-to-charges and a knowledgebase and a classifying algorithm that are dedicated to the discrimination of the subgroups of the group in question to be obtained.

On the basis of the knowledgebase and a classifying algorithm that are dedicated to the discrimination of groups and the knowledgebase and a classifying algorithm that are dedicated to the discrimination of the subgroups of at least one group of the groups in question, the method continues with a step of classifying an unknown microorganism.

This classifying step is for example implemented by a device, comprising:
- a mass spectrometer able to acquire at least one mass spectrum of the unknown microorganism;
- a computer system able to identify the unknown microorganism depending on the one or more mass spectra acquired by the spectrometer, said system comprising:
  a computer memory storing at least:
    the per-microorganism-group classifying model and knowledgebase;
    the per-microorganism-subgroup classifying model and knowledgebase;
    the adjusting model for correcting mass-to-charge offsets;
    computer instructions for producing a list of peaks on the basis of the acquired mass spectrum;
    computer instructions for classifying the unknown microorganism into a group depending on the produced list of peaks according to said per-group classifying model and said per-group knowledgebase;
    computer instructions for adjusting the list of peaks according to the adjusting model;
    computer instructions for classifying the microorganism into a subgroup depending on the adjusted list of peaks according to said per-subgroup classifying model and said per-subgroup knowledgebase;
  a microprocessor-based computer unit for implementing computer instructions stored in the computer memory so as to classify the microorganism into a group and a subgroup;
a computer memory for storing the result of the classification and/or a display screen for displaying the result of the classification.

The method therefore continues, in FIG. 1, with a step 300 of per-group classification. As described above, this step is based on the per-group knowledgebase, and the associated per-group classifying algorithm, which already exist or are constructed on the basis of a set of spectra of microorganisms the groups of which have been identified beforehand.

Figure 3C:
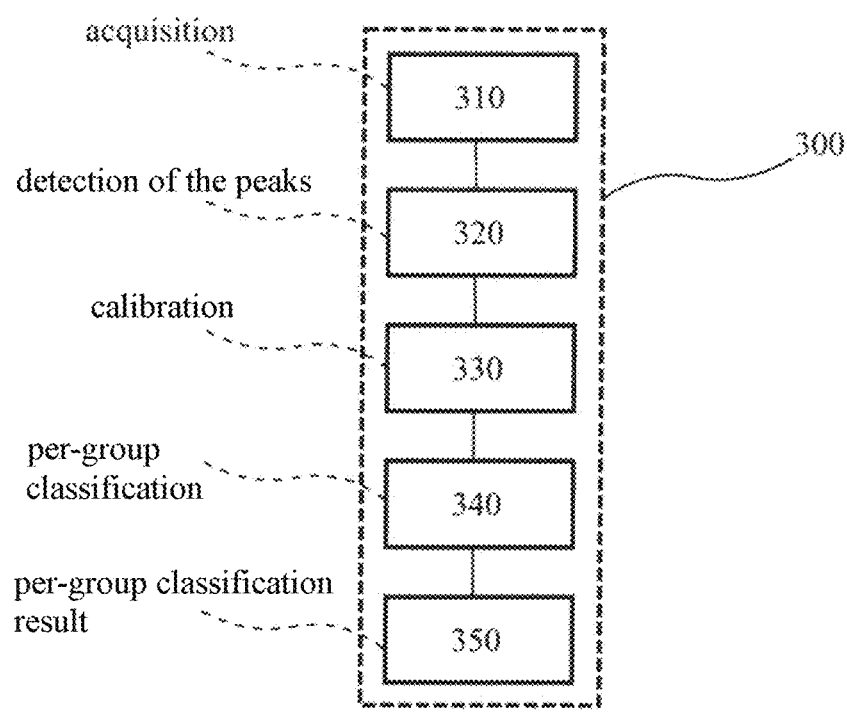
FIG. 3c is a flowchart of step 300 of the method according to the invention.

The per-group classifying step 300 starts, according to FIG. 3c, with a step 310 of acquiring at least one mass spectrum of said unknown microorganism. The step 310 starts with the preparation of a sample of the unknown microorganism to be identified, followed by the acquisition of one or more mass spectra of the prepared sample by means of a mass spectrometer, for example a MALDI-TOF spectrometer. This step is carried out in a similar way to step 110.

Following the acquiring step, the method continues with a step 320 of detecting the peaks of the spectra in a similar way to step 120 and of external or internal calibration 330 of these spectra, in a similar way to step 130. This step aims to obtain an alignment of the peaks allowing the classification into a group of said microorganism. As described above, external calibration consists in adjusting the m/z axis of the mass spectra of a reference sample, the content of which is known and which is placed at a different point on the plate to the sample, so that the observed peaks coincide with their theoretical position. This step is thus carried out in a similar way to step 130, the peaks of the spectrum of the unknown microorganism being realigned depending on the transformation applied to the spectrum of the calibrator.

Following this step, the method comprises a step 340 of classifying the one or more obtained lists of peaks. The per-group classifying algorithm, in relation with the associated per-group knowledgebase is implemented to do this. One or more groups (family, germ, species, etc.) are thus identified for the analyzed sample. Advantageously and in order to improve the per-group classifying step, this step may be preceded by a step of controlling the quality of the spectra in a similar way to step 140 and optionally by a step of discretizing the masses-to-charges, which step is similar to step 150, and/or by a step of processing the intensities, which is similar to step 155.

Alternatively, the step 340 may not be carried out in the case where the group of the analyzed microorganism is known that the subgroup is unknown. In this case, the method continues directly to step 350.

In a following step 350, a result of the classifying step is obtained, for example in the form of a score rating the probability that the unknown microorganism belongs to one or more groups. In the case where the retained group or at least one of the retained groups is represented in the per-subgroup knowledgebase, the method according to invention continues with a per-subgroup classifying step 400.

As described above, this step is based on the constructed per-subgroup knowledgebase and on the associated per-subgroup classifying algorithm, which were obtained on the basis of a set of spectra of microorganisms the groups and subgroups of which were identified beforehand.

Figure 3D:
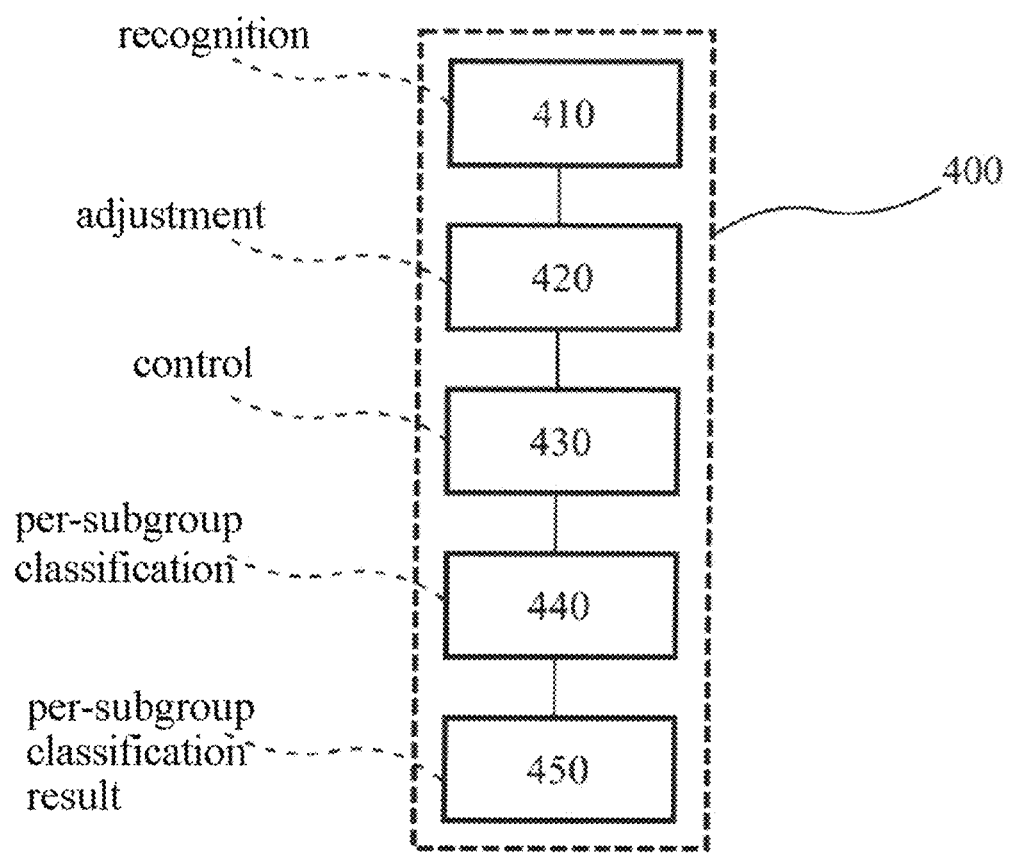
FIG. 3d is a flowchart of step 400 of the method according to the invention.

According to FIG. 3d, the per-subgroup classifying step 400 thus starts with a step 410 of recognizing a classification result of step 350 of a group for which a per-subgroup knowledgebase and a per-subgroup classifying algorithm exist. For example, a taxonomic group containing the species *Escherichia coli* and the genus *Shigella* may be associated with a taxonomic per-subgroup knowledgebase separating the non-O157 *Escherichia coli* (subgroup A), the O157 *Escherichia coli* (subgroup B), the species of *Shigella*: *Shigella dysenteriae* (subgroup C), *Shigella flexneri* (subgroup D), *Shigella boydii* (subgroup E), *Shigella sonnei* (subgroup F), etc. . . . .

The following step 420 then consists in adjusting the masses-to-charges of the list of peaks obtained following step 330 using the model obtained following step 260, and reference masses-to-charges, which are characteristic of the group and defined in step 240 or reference masses-to-charges, which are characteristic of the group and retained following step 250. In the case where a second adjusting model has been created, the list of peaks is then adjusted a second time using the adjusting model obtained following step 270, the characteristic masses-to-charges used then being those of the second model. In the same way, in the case where an n-th adjusting model has been created, the list of peaks is then adjusted an n-th time using the adjusting model obtained following step 270, the characteristic masses-to-charges used then being those of the n-th model.

Optionally, the method may continue with a step 430 of controlling the quality of the adjustment of the masses-to-charges. To do this, a number (or a percentage) of the reference masses-to-charges detected in the one or more acquired spectra may be defined as necessarily higher than a given threshold. Alternatively, or in addition, a root-mean-squared error (RMSE) between the theoretical position of each reference mass-to-charge and the position after adjustment of these masses-to-charges in the one or more acquired spectra may be defined as necessarily lower than a given threshold. The root-mean-squared error may thus be computed in a conventional way with the following equation:

$$RMSE = \sqrt{\frac{1}{L}\sum_{l=1}^{L}(\hat{R}(l) - R(l))^2}$$

where:
{R(l)}, l={1, . . . L} is the list of the L reference masses-to-charges for which a peak was observed in the spectrum in question.
f being the adjusting model obtained following step 260 and optionally 270,
$\hat{R}(l)$ being the adjusted mass-to-charge obtained with $\hat{R}(l)=f(R(l))$.

Following step 420 or 430, the method continues with a step 440 of classifying the adjusted spectrum on the basis of the per-subgroup knowledgebase and the classifying algorithm allowing subgroups learned and defined beforehand to be discriminated.

Advantageously and in order to improve the per-subgroup classifying step, this step may be preceded by a step of discretizing the masses-to-charges, which step is similar to the step 150, and/or a step of processing intensities, which step is similar to step 155.

In a following step 450, a result of the per-subgroup classifying step is obtained, for example in the form of a score rating the probability that the unknown microorganism belongs to one or more subgroups.

The result of the per-group and per-subgroup classifications, advantageously with their classification scores, is stored in a computer memory and/or displayed on a screen for the attention of the user.

Example of a Per-Subgroup Classification for a Group Formed by the Species *Escherichia coli* and the Genus *Shigella*.

The method according to the invention is applied to the classification of serogroups of the species *Escherichia coli* and of the species of *Shigella*. The method thus aims to distinguish subgroups depending on their pathogenicity.

The method uses a MALDI-TOF VITEK® MS (bioMérieux, France) mass spectrometer sold by the applicant and comprising a VITEK® MS v2.0.0 per-group knowledgebase, also called the VITEK® MS v2.0.0 database. The VITEK® MS apparatus also comprises an associated per-group classifying algorithm using a multi-variant classification, which algorithm is associated with the per-group knowledgebase. A score belonging to each of the groups is obtained following the step of classifying by means of the algorithm a spectrum of an unknown microorganism.

The method according to the invention thus allows a two-step (per-group then per-subgroup) classification to be proposed that can be performed routinely on a mass-spectrometry apparatus. Firstly, the group, here a species-level taxonomic group, will be identified and, in the case of the *Escherichia coli/Shigella* group, a second per-subgroup classifying level is proposed to differentiate the 4 species of *Shigella* of said group from the O157 serogroup of the species *Escherichia coli* and the non-O157 serogroups of the species *Escherichia coli*.

A first batch A of 116 strains of microorganisms, in which the *Escherichia coli* and *Shigella* group and the subgroups are identified with conventional phenotypic and serotype classifying techniques, is created. This batch will be used for the construction of one knowledgebase and one classifying model per reference subgroup.

This batch A contains:
60 strains of non-O157 *Escherichia coli* (reference esh-col) forming the subgroup A
8 strains of O157 *Escherichia coli* (reference esh-o157) forming the subgroup B
12 strains of *Shigella dysenteriae* (reference shg-dys) forming the subgroup C
12 strains of *Shigella flexneri* (reference shg-flx) forming the subgroup D
12 strains of *Shigella boydii* (reference shg-boy) forming the subgroup E
12 strains of *Shigella sonnei* (reference shg-son) forming the subgroup F These 116 microorganisms are not distinguished by the current VITEK® MS apparatus, the classifying algorithm of the apparatus thus classifying them into the group "*Escherichia coli/Shigella*" of the associated knowledgebase.

In order to proceed to the acquisition of the spectra of microorganisms of the batch A by mass spectrometry, the samples containing these microorganisms are prepared according to a conventional protocol:
Sampling of a colony after culture on agar growth medium using a broth
Suspending the colony in a 2 mL Eppendorf tube containing 300 µL of demineralized water
Adding 0.9 mL of absolute ethanol and mixing (vortex)
Centrifuging for 2 min at 10000 rpm
Removing supernatant using a pipette
Adding 40 µL of 70% formic acid and mixing (vortex)
Adding 40 µL of acetonitrile and mixing (vortex)
Centrifuging for 2 min at 10000 rpm
Depositing 1 µL of supernatant
Drying
Adding 1 µL of HCCA matrix An amount of each sample of each strain is deposited on a Maldi plate intended to be used with the VITEK® MS apparatus. The acquisitions are carried out in duplicate or quadruplicate. The acquisition is carried out using the LaunchPad V2.8 software package and with the following parameters:
Linear mode
Rastering: Regular circular
100 profiles per sample
5 irradiations per profile
Acquisition between 2000 and 20000 thomsons
Auto-quality parameter activated Following the acquisition of these spectra, the VITEK® MS apparatus performs the preprocessing and external calibration on the basis of the acquisition of a spectrum of a standard *Escherichia coli* strain (ATCC 8739) deposited in the location reserved for the calibration of the acquisition group. Once the spectrum of the standard strain has been acquired, the presence of 11 reference peaks corresponding to characteristic masses-to-charges of *Escherichia coli* is sought, with a tolerance of 0.07% around the expected position of the peaks. If at least 8 peaks from the 11 are found in the expected position interval, the peaks of the spectrum of the standard strain will be realigned depending on their reference position. The obtained transformation is used to realign the acquired spectra of the samples.

A total of 388 spectra corresponding to the 116 strains of the group of batch A thus allow a group-level knowledgebase and an associated classifying algorithm to be created. In order to confirm that the microorganisms of batch A are not distinguished by the apparatus and belong to the same group for the VITEK® MS v2.0.0 database and the associated algorithm, a per-group classifying step is carried out. The results of this classification for batch A are given in table 4 below:

TABLE 4

| Samples of batch A | Wrong group identified | No group identified | Escherichia coli/Shigella group | Total |
|---|---|---|---|---|
| esh-col | | | 192 | 192 |
| esh-o157 | | | 31 | 31 |
| shg-boy | | | 39 | 39 |
| shg-dys | | | 32 | 32 |
| shg-flx | | 1 | 46 | 47 |
| shg-son | | | 47 | 47 |
| Total | 0 | 1 | 387 | 388 |

99.7% of the spectra of batch A are correctly predicted as belonging to the *Escherichia coli/Shigella* group of the VITEK® MS v2.0.0 database. A single spectrum obtained from one strain of the species *Shigella flexneri* is not identified, although of good quality. It is nonetheless kept for the construction of the subgroup-level knowledgebase in the following steps.

On the basis of this base of 388 spectra corresponding to batch A and to the *Escherichia coli/Shigella* group, a subgroup-level knowledgebase and an associated classifying method are created.

To do this, the positions of the masses-to-charges of the detected peaks are adjusted in two adjusting steps by virtue of the successive construction of two adjusting models. In a first adjusting step, which is carried out in a similar way to steps 230, 240 and 260, 10 characteristic masses-to-charges of the group, which are known beforehand, for the *Escherichia coli/Shigella* group, and located between 4000 and 10000 Th, and corresponding to the masses-to-charges of the calibrator, are sought in the 388 spectra. The tolerance around the position of these masses-to-charges in each of the acquired spectra is set to t=0.0005%. On the basis of the observed position of these masses-to-charges and their theoretical position, a linear-regression model is computed in order to realign them with their theoretical position. The obtained transformation is also applied to all the peaks of each of the acquired spectra.

Following this first step, a second adjusting step 270 is carried out via an adjusted 2nd-order polynomial-regression model on a reference mass-to-charge list that is statistically determined according to the method described in step 240. To do this, each of the spectra adjusted following the first adjusting step is discretized in the range of masses-to-charges of interest with pitches of 1 Th between 3000 and 6000 Th, of 2 Th between 6000 and 10000 Th and of 3 Th between 10000 and 20000 Th. Each spectrum is thus discretized into 8366 mass-to-charge intervals. The presence or absence of peaks is sought with a tolerance of 0.0003% around each mass-to-charge m(i) defined by the discretization according to the method described in step 242. The masses-to-charges m(i) thus obtained are then filtered depending on the frequency of presence of peaks for each of the subgroups according to the method described in step 243. 133 masses-to-charges with a minimum frequency of presence for each of the subgroups of 60% are thus retained. This allows masses-to-charges that are particularly characteristic of the group to be selected.

The position of these masses-to-charges is then approximated according to a statistical model of the position of the retained masses-to-charges. This step corresponds to the described step 244.

On the basis of the corrected positions, identical or almost identical approximate masses-to-charges are removed, in order to retain a list of 46 unique masses-to-charges, which list is characteristic of the group. 2 masses-to-charges are considered to be identical after approximation if the observed discrepancy between the 2 masses-to-charges is smaller than 0.1 Th. This step corresponds to the described step 245.

TABLE 5

| Position of the selected masses-to-charges (initial discretization) | Approximate position of the masses-to-charges (after adjustment) | Position of the retained masses-to-charges |
|---|---|---|
| 5338 | 5339.8 | 5339.8 |
| 5340 | 5339.8 | |
| 5342 | 5339.8 | |
| 5378 | 5381.2 | 5381.2 |
| 5380 | 5381.2 | |
| 5382 | 5381.2 | |
| 5384 | 5381.2 | |
| 5394 | 5397.4 | 5397.4 |
| 5396 | 5397.4 | |
| 5398 | 5397.4 | |

Table 5 above illustrates, in the interval of masses-to-charges 5338 to 5398 Th, the position of the selected masses-to-charges in the discretized space of the masses-to-charges, the approximate value of the same masses-to-charges and the final list of the masses-to-charges retained after removal of identical masses-to-charges.

Next, an adjusting step is thus carried out in a similar way to step 270 on the basis of the positions of the retained masses-to-charges. An optional step allowing the list of reference masses-to-charges to be controlled and optimized, which step is based on the obtained adjustment quality allows a shorter list of 37 final reference masses-to-charges to be retained. This step is based on criteria such as defined in step 265. Five masses-to-charges are removed because they have, for at least one of the subgroups either a percentage of presence of a peak after adjustment lower than 60%, or a median of the residues higher than 1 Th, or an interquartile interval of the residues higher than 2 Th. On the basis of this shorter list of reference masses-to-charges, the method continues with a readjustment of all the masses-to-charges of the lists of peaks of the group.

Figure 8A:
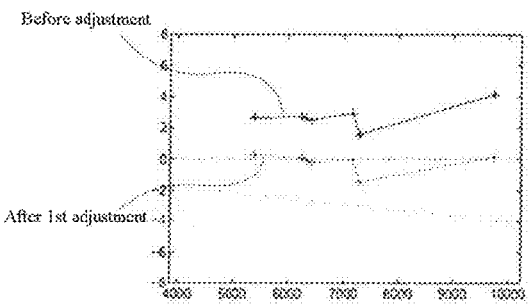
FIGS. 8a and 8b are a chart of the result of a first adjustment and a second adjustment according to the invention
Figure 8B:
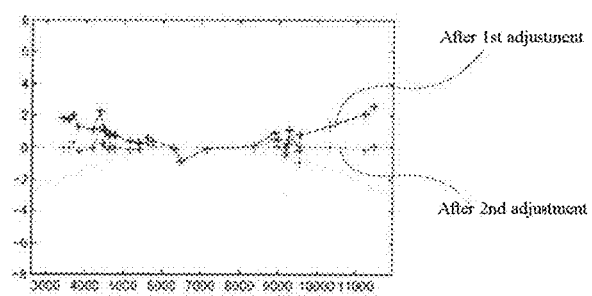

According to FIG. 8a, the method comprises a first adjustment similar to step 260 via an adjusted linear-regression model on the reference masses-to-charges detected only between 5000 and 10000 Th because of a high initial offset of the masses-to-charges. The correction of the masses-to-charges is extrapolated beyond this mass-to-charge interval. The use initially of a linear model allows the error in the extrapolation of the list of masses-to-charges of the spectrum in question to be limited. According to FIG. 8b, the method comprises a second adjustment similar to step 270 via an adjusted 2nd-order polynomial-regression model on the masses-to-charges detected between 3000 and 12000 Th, allowing the position of the peaks of the spectrum in question to be more finely adjusted over a wider mass-to-charge range.

FIG. 9a illustrates, for a mass-to-charge range, the observed position of the peaks among all the spectra of the group and corresponding subgroup before adjustment. FIG.

9b illustrates the position of the same peaks after a second adjustment, demonstrating the quality of the adjustment carried out and the relevance of the mass-to-charge selected as reference mass-to-charge.

The precision claimed by the manufacturer after external calibration of the VITEK® MS apparatus is 400 ppm, i.e. a precision in thomson of about 1.2 Th at 3000 Th/4.4 Th at 11000/Th. The precision in thomson observed after external calibration, FIG. 10a, is, to give the median quantity, about the claimed precision for the set of data in question, namely about 1.2 Th for the masses-to-charges around 3000 Th and about 3 Th for the masses-to-charges around 11000 Th. After the second adjustment of the masses-to-charges with the method according to the invention, FIG. 10b, the precision is about 0.12 Th at 3000 Th and 0.44 Th at 11000 Th, i.e. a precision of about 40 ppm. This increase in precision after adjustment with the method according to the invention demonstrates the relevance of the selected reference masses-to-charges and the quality of the adjustment carried out.

A dedicated knowledgebase and a dedicated classifying algorithm allowing subgroups of the *Escherichia coli/Shigella* group to be discriminated on the basis of the lists of peaks of the spectra having undergone the adjustment described above are then constructed following the method described in steps 280 and 290.

To do this, a knowledgebase and a dedicated classifying algorithm allowing the following six subgroups to be distinguished are constructed Non-O157 *Escherichia coli*, subgroup A
O157 *Escherichia coli*, subgroup B
*Shigella dysenteriae*, subgroup C
*Shigella flexneri*, subgroup D
*Shigella boydii*, subgroup E
*Shigella sonnei*, subgroup F By way of example, FIG. 11a illustrates, for a mass-to-charge range containing a mass allowing the O157 *Escherichia coli* subgroup to be discriminated from the other subgroups, the observed position of the peaks, among all the spectra of the group and corresponding subgroups before adjustment. FIG. 11b illustrates the position of the same peaks after a second adjustment, demonstrating that it is then possible to use the presence/absence of the peak at 10139 Th with a tolerance of +/−2 Th to detect the O157 *Escherichia coli* subgroup from which this peak is absent.

In order to verify the capacity of the classifying model and the associated per-subgroup knowledgebase to classify microorganisms into subgroups, a second batch B of 31 strains identified as belonging to the *Escherichia coli/Shigella* group and the subgroups of which are determined via conventional analyzing methods is also formed.

This batch B, which is called the evaluation batch, contains 31 strains of Shiga Toxin *Escherichia coli* (STEC) of 6 different O serotypes: O26, O45, O103, O111, O121 and O145.

The sample preparation protocol is identical to that used above. Two spectra are acquired per strain in order to obtain a list of 62 spectra distributed according to table 6 below.

TABLE 6

| O serotype/ ATCC number | Number of spectra | O serotype/ ATCC number | Number of spectra | O serotype/ ATCC number | Number of spectra |
|---|---|---|---|---|---|
| O103 | 10 | O121 | 10 | O26 | 10 |
| BAA-2199 | 2 | BAA-2187 | 2 | BAA-2181 | 2 |
| BAA-2200 | 2 | BAA-2203 | 4 | BAA-2186 | 2 |

TABLE 6-continued

| O serotype/ ATCC number | Number of spectra | O serotype/ ATCC number | Number of spectra | O serotype/ ATCC number | Number of spectra |
|---|---|---|---|---|---|
| BAA-2207 | 2 | BAA-2220 | 2 | BAA-2188 | 2 |
| BAA-2210 | 2 | BAA-2221 | 2 | BAA-2204 | 2 |
| BAA-2213 | 2 | | | BAA-2205 | 2 |
| O111 | 12 | O145 | 10 | O45 | 10 |
| BAA-179 | 2 | BAA-1652 | 2 | BAA-2185 | 2 |
| BAA-180 | 4 | BAA-2192 | 2 | BAA-2189 | 2 |
| BAA-184 | 2 | BAA-2211 | 2 | BAA-2191 | 2 |
| BAA-2180 | 2 | BAA-2222 | 2 | BAA-2198 | 2 |
| BAA-2201 | 2 | BAA-2223 | 2 | BAA-2202 | 2 |

These strains are in particular identified in the publication American Type Culture Collection ATCC: "Big Six" Non-o157 Shiga Toxin-Producing *Escherichia coli* (STEC) Research Materials.

In order to confirm that the microorganisms of the batch B are not distinguished by the apparatus and the knowledgebase of the prior art and thus belong to the same group, a per-group classifying step according to step 300 is carried out. The results of this classification for the batch B are given in table 7 below:

TABLE 7

| Samples of batch B | Wrong group identified | No group identified | *Escherichia coli/ Shigella* group | Total |
|---|---|---|---|---|
| esh-col O103:H11 | | | 2 | 2 |
| esh-col O103:H2 | | | 4 | 4 |
| esh-col O103:H25 | | | 4 | 4 |
| esh-col O111:H8 | | | 12 | 12 |
| esh-col O121:H19 | | | 10 | 10 |
| esh-col O145:H25 | | | 2 | 2 |
| esh-col O145:H48 | | | 2 | 2 |
| esh-col O145:Nonmotile | | | 6 | 6 |
| esh-col O26:H11 | | | 10 | 10 |
| esh-col O45:H2 | | | 10 | 10 |
| Total | 0 | 0 | 62 | 62 |

100% of the spectra are correctly predicted as belonging to the *Escherichia coli/Shigella* group by the VITEK® MS v2.0.0 knowledgebase and classifying algorithm.

All of the spectra of batch B are kept for the evaluation of the per-subgroup classifying algorithm and knowledgebase according to step 400.

The method according to the invention is implemented on the basis of the per-subgroup knowledgebase created beforehand and the associated classifying algorithm. The expected classification for the batch B is a result of the non-O157 *Escherichia coli* subgroup type.

To do this, the masses-to-charges of the list of peaks obtained during the group-level classifying step are adjusted using first and second models for adjusting the masses-to-charges, which models have been defined beforehand.

In order to improve the performance of the classification, and optionally, a quality-control is carried out on the adjustment of the masses-to-charges. The quality criteria defined in order to ensure the quality of the adjustment of the masses-to-charges of each spectrum are the following:

For the spectrum in question, at least 28 masses-to-charges must be detected among the 37 predefined reference masses-to-charges and the root-mean-squared error (RMSE) between the theoretical position of each reference mass-to-charge and the position after adjustment of these masses-to-charges in the acquired spectra must be lower than 1.

5 spectra do not meet these criteria but 58 do meet them.

The 58 retained spectra are classified on the basis of the knowledgebase and classifying algorithm allowing classification at the level of the subgroups defined beforehand. As illustrated in FIG. 12, all the spectra are correctly identified as belonging to the non-O157 *Escherichia coli* subgroup with high scores. In addition, the second best score obtained in another subgroup is very clearly lower, this ensuring the robustness of the classification.

The invention claimed is:

1. A method for identifying by mass spectrometry an unknown microorganism subgroup among a set of reference subgroups, each subgroup belonging to one species among a set of reference species, the method including:
constructing one knowledgebase and one classifying model per associated species on the basis of a set of learning spectra of microorganisms identified as belonging to the set of reference species;
constructing one knowledgebase and one classifying model per associated subgroup on the basis of the acquisition of at least one set of learning spectra of microorganisms identified as belonging to the subgroups of the species, comprising, for each species of the set of reference species:
constructing an adjusting model allowing mass-to-charge offsets of the learning spectra of the subgroups of the species to be corrected on the basis of reference masses-to-charges that are common to the various subgroups of the species;
adjusting the masses-to-charges of all of the lists of peaks of the learning spectra of the subgroups of the species using the adjusting model; and
constructing one classifying model per subgroup and the associated knowledgebase on the basis of the adjusted learning spectra of the subgroups; and
classifying to a subgroup an unknown microorganism including:
acquiring at least one spectrum of the unknown microorganism;
classifying into a species the spectrum according to the per-species classifying models and the per-species knowledgebases;
adjusting the masses-to-charges of all of the list of peaks of the spectrum according to the adjusting model of the classified species, allowing mass-to-charge offsets of the spectrum of the unknown microorganism to be corrected; and
classifying the adjusted list of peaks into a subgroup of the classified species with the per-subgroup classifying models and the per-subgroup knowledgebases.

2. The identifying method as claimed in claim 1, wherein the constructing one knowledgebase and one classifying model per associated subgroup further comprises:
constructing a second adjusting model allowing mass-to-charge offsets of the acquired spectra to be corrected on the basis of reference masses-to-charges that are common to the various subgroups of the species; and
further adjusting the masses-to-charges of all of the lists of peaks of the adjusted learning spectra on the basis of the second adjusting model.

3. The identifying method as claimed in claim 1, comprising optimizing the list of the reference masses-to-charges, which is based on the quality of the adjustment obtained following at least one of (i) the adjusting the masses-to-charges of all of the lists of peaks of the learning spectra of the subgroups of the species; and (ii) the adjusting the masses-to-charges of all of the list of peaks of the spectrum according to the adjusting model of the species.

4. The identifying method as claimed in claim 1, wherein the known reference masses-to-charges that are common to the various subgroups of the species are selected by:
detecting the presence or absence of peaks around the reference masses-to-charges according to a tolerance factor; and
filtering the masses-to-charges depending on a frequency of the presence of the peaks for each of the subgroups and approximating the position of the reference masses-to-charges that remain after the filtering.

5. The identifying method as claimed in claim 4, wherein the filtering uses statistical criteria of the frequency of the presence of the peaks in each of the subgroups of the species.

6. The identifying method as claimed in claim 1, wherein the reference masses-to-charges that are common to the various subgroups of the species are deduced by:
discretizing the space of the masses-to-charges of each of the spectra of each subgroup;
detecting the presence or absence of peaks around the masses-to-charges defined by the discretizing step according to a tolerance factor;
filtering the masses-to-charges depending on the frequency of the presence of the peaks for each of the subgroups; and
approximating the position of the masses-to-charges that remain after the filtering.

7. The identifying method as claimed in claim 6, wherein the discretizing is carried out over an interval of masses-to-charges that is restricted with respect to the interval of masses-to-charges present in the at least one set of learning spectra of microorganisms identified as belonging to the subgroups of the species.

8. The identifying method as claimed in claim 4, wherein the approximating comprises seeking a position representative of the distribution of the positions of the peaks present around each of the masses-to-charges that remain after the filtering.

9. The identifying method as claimed in claim 1, wherein the constructing one knowledgebase and one classifying model per associated subgroup comprises discretizing the masses-to-charges of the at least one set of learning spectra of microorganisms identified as belonging to the subgroups of the species.

10. The identifying method as claimed in claim 1, wherein the constructing one knowledgebase and one classifying model per associated subgroup comprises processing the intensities of the at least one set of learning spectra of microorganisms identified as belonging to the subgroups of the species.

11. The identifying method as claimed in claim 1, wherein the constructing one knowledgebase and one classifying model per associated subgroup comprises controlling the quality of the at least one set of learning spectra of microorganisms identified as belonging to the subgroups of the species.

12. The identifying method as claimed in claim 1, wherein the parameters of the adjusting model are obtained with a robust estimating method.

13. The identifying method as claimed in claim 1, wherein the set of learning spectra of microorganisms identified as belonging to the set of reference species are directly used for the constructing one knowledgebase and one classifying model per associated subgroup, the species and subgroups of the learning microorganisms being known.

14. A device for identifying a microorganism by mass spectrometry, comprising:
- a mass spectrometer able to produce mass spectra of microorganisms to be identified; and
- a computing unit able to identify the microorganisms associated with the mass spectra produced by the spectrometer by implementing a method as claimed in claim 1.

* * * * *